United States Patent [19]

Shofner et al.

[11] Patent Number: 5,367,747
[45] Date of Patent: Nov. 29, 1994

[54] NEEDLE-BASED APPARATUS FOR INDIVIDUALIZING FIBERS AND OTHER TEXTILE ENTITIES FOR TESTING PURPOSES

[75] Inventors: Frederick M. Shofner; Mark G. Townes, both of Knoxville; Gordon F. Williams, Norris, all of Tenn.

[73] Assignee: Zellweger Uster, Inc., Knoxville, Tenn.

[21] Appl. No.: 999,305

[22] Filed: Dec. 31, 1992

[51] Int. Cl.$^5$ .................... D01B 3/04; G01L 5/04
[52] U.S. Cl. ........................ 19/65 R; 73/160
[58] Field of Search .............. 73/159, 160; 19/65 R, 19/115, 129 R

[56] References Cited

U.S. PATENT DOCUMENTS

| | | | |
|---|---|---|---|
| 2,098,781 | 11/1937 | Holdsworth | 19/129 |
| 2,299,983 | 10/1942 | Hertel | 234/1.5 |
| 2,404,708 | 7/1946 | Hertel | 19/115 |
| 3,057,019 | 10/1962 | Hertel | 19/65 R |
| 3,104,426 | 9/1963 | Wellman | 19/129 |
| 3,113,350 | 12/1963 | Selby | 19/240 |
| 3,153,812 | 10/1964 | Skakibara et al. | 18/1 |
| 3,276,071 | 10/1966 | Nagae et al. | 18/1 |
| 3,427,684 | 2/1969 | Tsien | 18/1 |
| 3,577,598 | 5/1971 | Schwarz | 19/65 R |
| 3,626,552 | 12/1971 | Walker et al. | 19/129 |
| 3,913,176 | 10/1975 | Grossi | 19/35 |
| 3,916,491 | 11/1975 | Kampf | 26/57 |
| 3,971,104 | 7/1976 | Turpie et al. | 19/115 |
| 4,070,732 | 1/1978 | Herubel | 19/236 |
| 4,169,301 | 10/1979 | Kaiser | 19/129 |
| 4,200,963 | 5/1980 | Kamfe et al. | 26/73 |
| 4,293,983 | 10/1981 | Van Deusen et al. | 19/127 |
| 4,384,392 | 5/1983 | Allen | 26/72 |
| 4,512,060 | 4/1985 | Shofner | 19/200 |
| 4,554,709 | 11/1985 | Bianchi | 19/218 |
| 4,703,431 | 10/1987 | Sako et al. | 364/470 |
| 5,167,150 | 12/1992 | Shofner et al. | 73/160 |
| 5,178,007 | 1/1993 | Ghosashi et al. | 73/160 X |
| 5,185,639 | 2/1993 | Toedtli et al. | 73/159 X |

FOREIGN PATENT DOCUMENTS 1242171  1/1969  United Kingdom .

Primary Examiner—Clifford D. Crowder
Assistant Examiner—John J. Calvert
Attorney, Agent, or Firm—Luedeka, Neely & Graham

[57] ABSTRACT

Disclosed are various needle-based devices for individualizing single fibers and other entities from a fibrous mass, particularly for testing purposes. In one embodiment, an accelerated pin drafting machine has a plurality of combing elements which sequentially pierce a fiber mat and move within a drafting zone with increasing distance between adjacent combing elements. The accelerated pin drafting machine in turn feeds a fiber individualizer. In another embodiment, a comb-like needle sampler is provided which moves past a perforated plate such that portions of fibrous material protruding through the perforations are loaded onto the needle sampler. An elastomer clamping feedroll moves against the needles to clamp the sample, and then rotates to gradually feed fibers from the sampler. As an alternative to the elastomer clamping feedroll, a clamping block presses against the needles, and the needles are slowly retracted to gradually release fibers. In a third embodiment, fibers protruding through a perforated plate are loaded onto a single needle, and the ends of the fibers are drawn into an airstream moving through a passage defined by a housing on either side of a fiber plate. The fiber plate subsequently engages the needle to clamp fibers in position and the housing retracts to expose the fiber plate for fiber preparation. Thereafter, a roll or apron feeds individual fibers from the fiber plate.

13 Claims, 22 Drawing Sheets

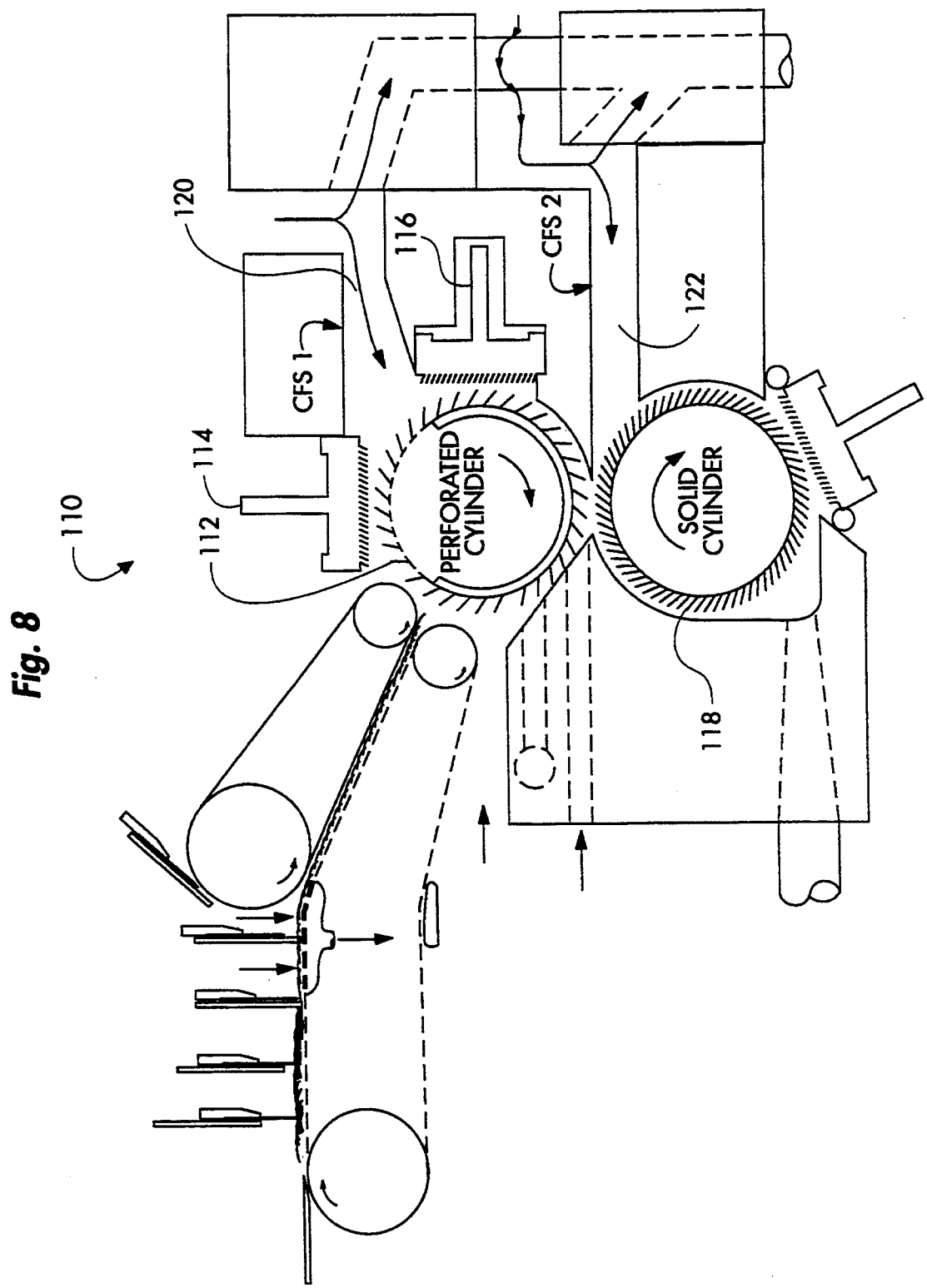

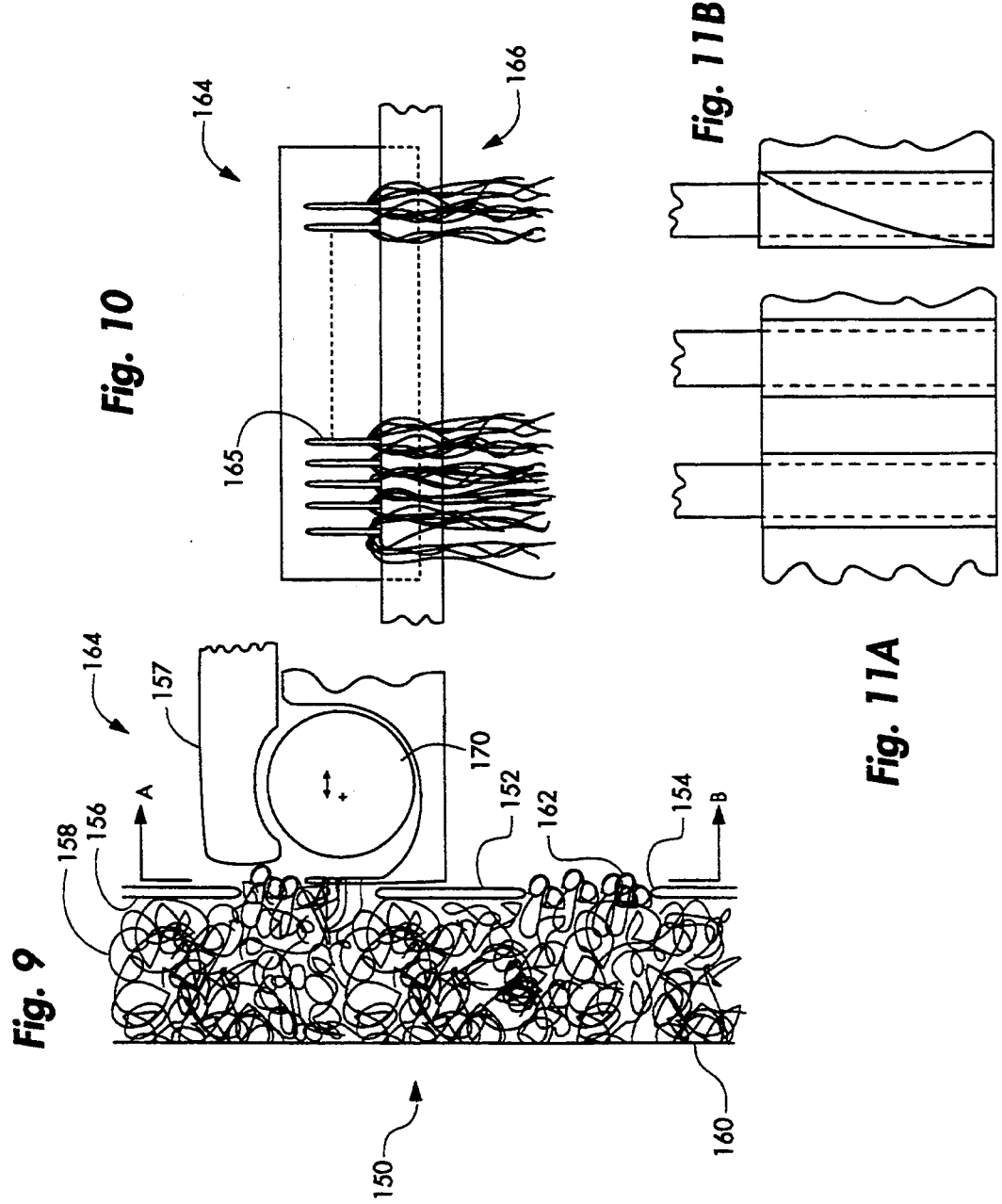

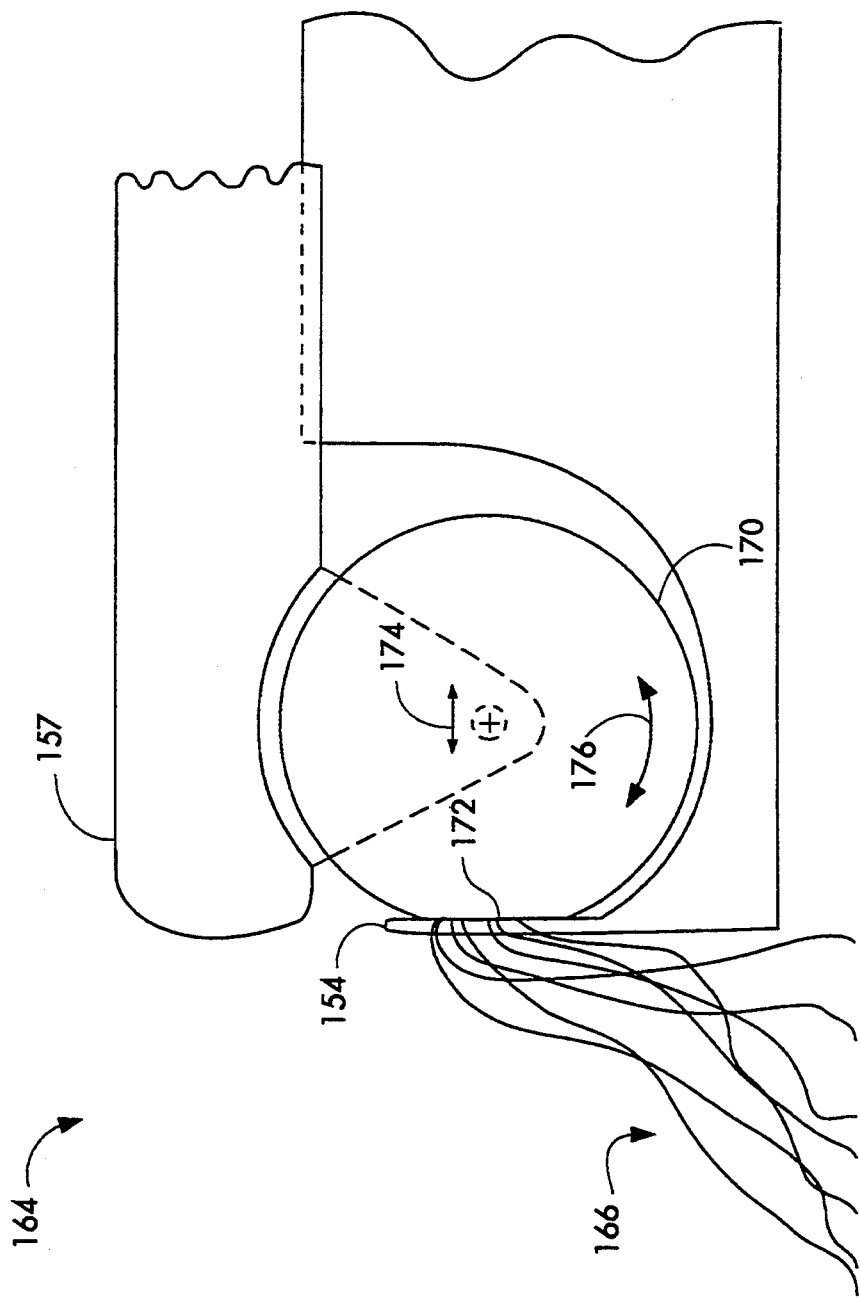

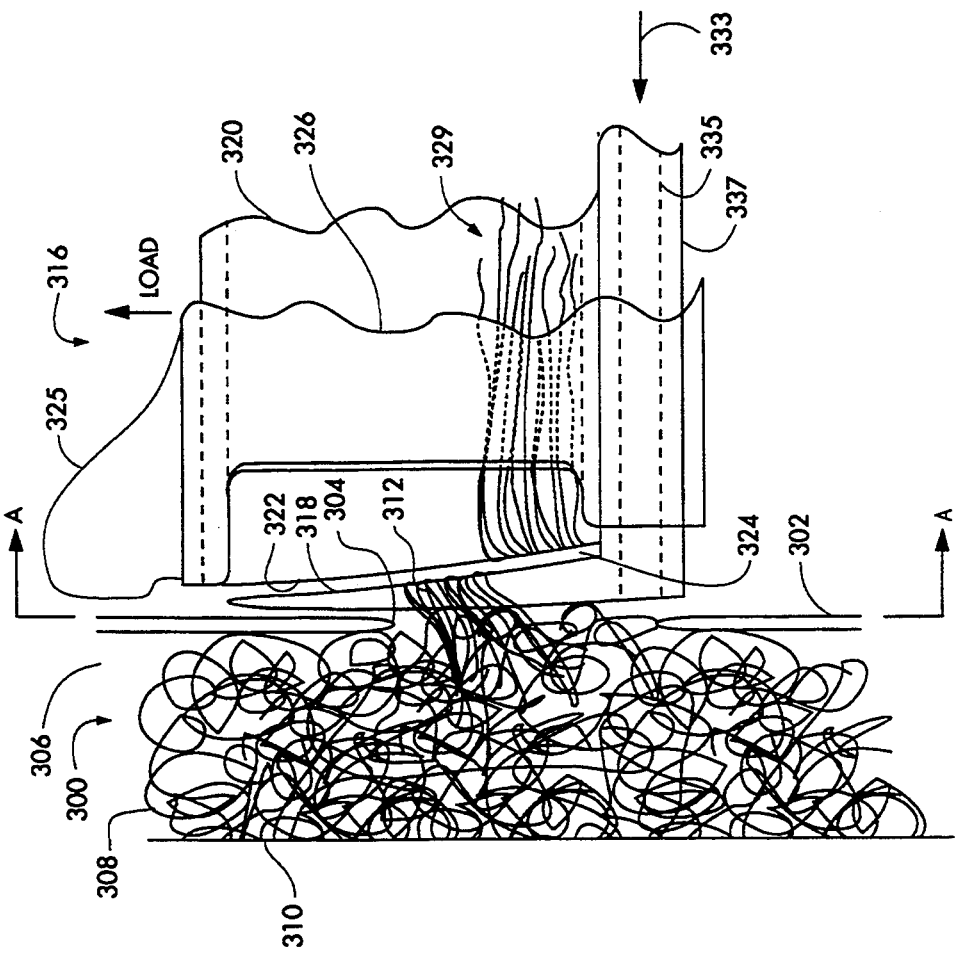

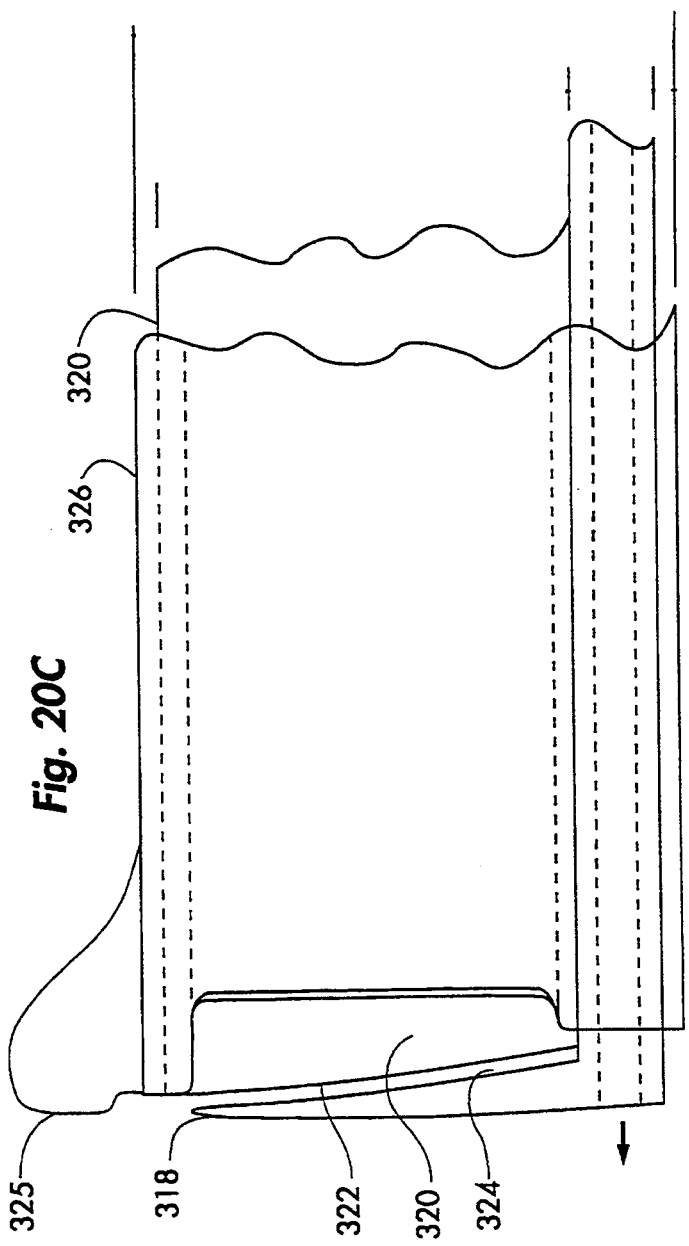

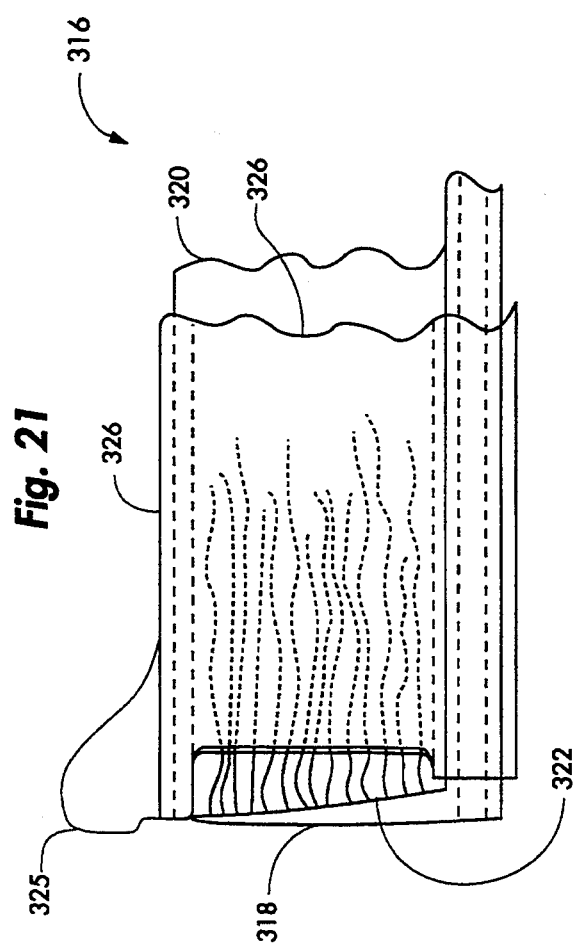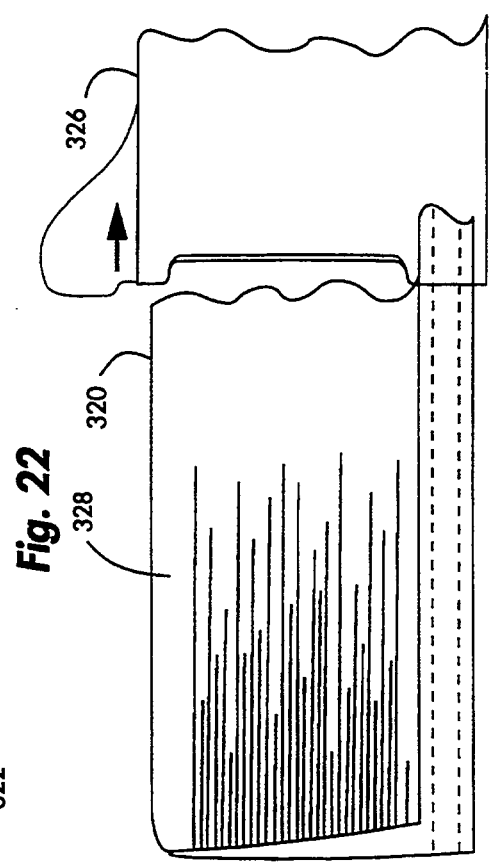
Fig. 21
Fig. 22

NEEDLE-BASED APPARATUS FOR INDIVIDUALIZING FIBERS AND OTHER TEXTILE ENTITIES FOR TESTING PURPOSES

FIELD OF THE INVENTION

The present invention relates generally to the testing of fiber samples and, more particularly, to needle-based apparatus for individualizing single fibers and other entities in textile fiber samples for testing purposes with a minimum of damage to the fibers, such as breakage.

BACKGROUND OF THE INVENTION

Testing of fiber samples, such as, but not limited to, cotton, is important for determining the market value of a particular batch of material, as well as for determining a suitable usage and what processing may be required in gins or spinning mills. Today, nearly 100% of the cotton grown in the United States is classed employing testing instruments. Testing includes determining such characteristics as fiber length, as well as the content of undesired textile entities such as trash and neps.

As a relatively early example, a comb-like device for preparing a sample of ginned cotton for measuring the fiber length thereof is disclosed in Hertel U.S. Pat. No. 2,404,708, which issued in 1946. That same inventor later developed what is now known as a Hertel needle sampler, disclosed in Hertel U.S. Pat. No. 3,057,019. The Hertel needle sampler is a comb-like device arranged for movement past a perforated plate which has a fibrous mass pushed against the opposite side so that portions of the fibrous mass protrude through the perforations and are loaded onto the needles. A screw-thread based locking device then retains the fibers on the needle sampler, forming what is known in the art as a tapered beard because the fibers are of varying lengths. The tapered beard is prepared by combing and brushing to parallelize the fibers, as well as to remove loose fibers. An automated version of the Hertel needle sampler is contained within and is a major element of fiber testing apparatus, known as the Model 900A High Volume Instrument (HVI). This apparatus has been manufactured by Spinlab, Inc., and is now manufactured by Zellweger Uster, Inc. in Knoxville, Tenn.

The tapered beard is then subjected to analysis. For example, an instrument known as a Fibrograph, formerly manufactured by Spinlab, Inc., and now by Zellweger Uster, Inc. in Knoxville, Tenn., is employed to optically determine various characteristics of the tapered beard, including the profile along its length. In addition, a separate test may be made of the strength of the tapered beard.

In some respects, the sample as taken by a Hertel needle sampler and the measurement of length and strength therefrom, are worldwide standards.

The approach just described involves collectively testing, essentially simultaneously, all of the fibers of a sample, assumed to be a representative sample. An alternative approach is to individualize and test single fibers and other textile entities, for example neps and trash. Testing single fiber entities can provide a better analysis. Thus, measuring directly, and at high speed, physical properties of single entities in a fiber sample results in basic measurements which provide more and better information which is needed in modern textile manufacturing. The measurements are more basic because single entities (single fibers, single neps, single trash particles, single microdust particles, etc.) are directly measured rather than indirectly by measuring bulk or bundle properties. Equally importantly, they are more basic because statistical distributions are easily formed with the aid of modern electronics technology.

However, such an approach requires means for individualizing single entities and feeding them one at a time into suitable analysis means for testing. A device for such isolation is generally termed a "fiber individualizer", and is generally so termed herein, although a more precise term is "entity individualizer" since, for purposes of testing, it is necessary to accurately determine the amount of neps and trash in a particular sample, in addition to characteristics of the fibers themselves.

An example of such single entity testing apparatus is disclosed in Shofner U.S. Pat. No. 4,512,060, which discloses what is termed in that patent a microdust and trash machine (MTM), and what has since become known as an advanced fiber information system (AFIS), currently manufactured by Zellweger Uster, Inc. in Knoxville, Tenn.

In one form, the AFIS machine separates fibers and neps into one airstream, and trash into another air stream. Optical-based sensors then measure the individual entities. Individual entities can be analyzed at rates as high as 1000 per second. An AFIS more particularly includes an aeromechanical separator or fiber individualizer; high speed single entity sensors; and a high information rate computer for data collection and analysis.

Improvements to the AFIS, particularly improved sensors where a single sensor analyzes neps, trash and fibers individualized all in one air stream are disclosed in Shofner et al application Ser. No. 07/493,961, filed Mar. 14, 1990, entitled "Electro-Optical Methods and Apparatus for High Speed, Multivariant Measurement of Individual Entities in Fiber or Other Samples", and in Shofner et al continuation-in-part applications Ser. No. 07/762,905, filed Sept. 19, 1991, entitled "Apparatus for Monitoring Trash in a Fiber Sample", and Ser. No. 07/962,898, filed Oct. 16, 1992, entitled "Apparatus and Method for Testing Multiple Characteristics of Single Textile Sample with Automatic Feed."

Individualized fibers may be however tested in a number of other ways, and the fiber individualizers of the present invention are not limited to any particular testing technique. For example, individualized fibers may simply be spread out on a horizontal surface which comprises a contrasting background, and optically imaged.

The fiber individualizer portion of an AFIS, such as is disclosed in U.S. Pat. No. 4,512,060, includes a cylindrical rotating beater wheel having projections which engage fibers of fibrous material fed to the beater wheel for testing. The beater wheels rotates at typically 7,500 rpm, with a circumferential velocity of 5,000 FPM, and is similar to the licker-in of a conventional carding machine, or the beater stage of an open-end spinning head, with the exception that the AFIS beater wheel includes perforations which allow radially inward airflow.

One disadvantage of the fiber individualizer disclosed in U.S. Pat. No. 4,512,060 is that fibers are subject to breakage as they are fed from a fibrous mass and abruptly engaged by the pins of the rotating beater wheel. In particular, fiber damage is caused by the interaction of fiber held between a feed plate/feed roll arrangement and the pinned cylinder rotating at high speed. The resultant action does liberate single fibers from the sample fiber mass but it also causes fiber breakage, and breaks up some foreign matter in the fiber (i.e. cotton trash). This action of restraining a portion of the fiber while quickly accelerating another portion of the fiber is well represented in mill processes (especially in opening, cleaning and carding), and leads to similar problems. Further damage results as fibers, in relatively random orientations, are carried past card flats.

The damage is, in general, more pronounced in a sample containing randomly oriented, highly entangled fibers (bale stock or card mat) than it is in a sample containing disentangled, parallel oriented fibers (sliver). Thus, it has been observed that, when parallelized fibers, such as sliver, are fed to the rotating beater wheel of an AFIS, far less fiber breakage occurs. However, bulk fiber for testing is generally not available in parallelized form.

Another disadvantage of the AFIS Fiber Individualizer is that it requires an elongated, sliver-like sample. For testing fibrous masses, wherein the fibers are randomly oriented, this elongated sample must be currently hand-formed. It follows that alternative means for collecting representative samples and introducing them into AFIS is needed. This need is rapidly increasing now, as automation requirements increase.

Several processes are known for parallelizing fibers, and an important one of such process is known as drafting or drawing, which particularly is employed in production environments, not in testing environments and not for randomly oriented fibrous masses.

Other forms of drafting are known, such as apron drafting or Casablanca drafting wherein a web of fibers, already parallelized and partially drafted, is transported between a pair of belt-like moving aprons and then through a pair of rollers turning at a higher speed. In some situations, such as is disclosed in U.K. Pat. No. 1,242,171, fibers are released from the roller pair essentially one at a time into an airstream.

SUMMARY OF THE INVENTION

Accordingly, it is an object of the invention to provide improved methods for individualizing fibers and other entities, such as trash and neps, from a sample of bulk fiber material, for testing purposes.

It is another object of the invention to provide a means for parallelizing fibers for feeding into an existing AFIS machine to minimize fiber breakage within the fiber individualizer portion of the AFIS.

It is another object of the invention to provide an improved method and apparatus which, at least, receives a mass of entangled, disoriented fibers and produces, at an output, a flow of substantially disentangled, parallel oriented and undamaged fibers, particularly for delivering to an AFIS.

Very briefly, the invention provides a number of approaches employing various needle and pin devices for individualizing single fibers and other entities, specifically for testing purposes.

More particularly, in accordance with a first embodiment of the invention, needle-based apparatus for isolating single fibers includes a pin drafting type machine having an input and an output, and a plurality of combing elements arranged to pierce a fiber mat presented to the input and to move in a direction from input to output with increasing distance between adjacent combing elements so as to transport and draft the fiber mat. The pin drafting machine may be termed an accelerated pin drafting (APD) machine because, in continuous operation, the combing elements move with acceleration within a drafting zone of the pin drafting machine.

The apparatus additionally includes a fiber individualizer arranged to receive the fiber mat from the pin drafting machine and to individualize the fibers.

The fiber individualizer may comprise further drafting apparatus, such as a feeder for engaging the fiber mat and for subsequently releasing fibers substantially individually into an air stream, such as a pair of rollers. Alternatively, the fiber individualizer may comprise the cylindrical rotating beater wheel of an AFIS machine, as is described above.

In accordance with a second embodiment of the invention, needle-based apparatus for isolating fibers and other entities from a loose mass is based on the Hertel needle sampler referred to hereinabove, but includes means for feeding fibers and other entities from the needle sampler for individual analysis, in contrast to analyzing a tapered beard.

In particular, such apparatus includes a sample holder with a plate having perforations and a sample side against which a loose mass of fibrous material is pressed such that portions of the fibrous material project through the perforations, and a comb-like needle sampler having a plurality of needle elements in a row and arranged for generally parallel movement relative to the plate on the other side of the plate so as to load fibers from the projecting portions onto the needle sampler. The apparatus additionally includes an element arranged to selectively engage the needle elements along at least a portion of their lengths for clamping loaded fibers on the needle sampler and for permitting subsequent gradual release of fibers from the needle sampler. In one form, this element takes the form of an elastomer clamping feedroll which moves against the needle elements for clamping loaded fibers, and subsequently rotates to gradually feed fibers from the needle elements. Alternatively, a clamping block may be provided which moves relative to a needle element against the needle elements for clamping loaded fibers, and the needle elements subsequently retract to gradually release fibers.

In one embodiment based on the Hertel needle sampler, the apparatus includes a cylindrical rotating beater wheel, such as the input stage of an AFIS, having projections for engaging fibers as they are released from the needle sampler.

In a variation of the second embodiment, the apparatus includes a drum in the form of an at least partially hollow cylinder rotatable about its axis, the drum including a sample holder portion including a circumferential cylindrical wall segment having perforations, and an interior side against which a loose mass of fibrous material is pressed such that portions of the fibrous material projects radially outwardly through the perforations, and a card doffer wire portion of the bucket including a circumferential segment having doffer wire on a surface of the circumferential segment projecting radially outwardly. The apparatus additionally includes a comb-like needle sampler having a plurality of needle elements positioned adjacent the bucket such that fibers from the projecting portions are loaded onto the needle sampler as the cylindrical wall segment of the sample holder portion rotates in a first direction past the needle sampler. The apparatus also has an element arranged to selectively engage the needle elements along at least a portion of their lengths for locking loaded fibers on the needle sampler and for permitting subsequent gradual release of fibers from the needle sampler onto the card doffer wire as the circumferential segment of the card doffer wire portion rotates in the first direction past the needle sampler.

Means are provided for removing fibers from the card doffer wire, such as a cylindrical rotating beater wheel, which may be the input element of an AFIS, or a brush, positioned adjacent the drum and having projections for engaging and removing fibers from the card doffer wire as the card doffer wire portion rotates in a second direction past the cylindrical rotating beater wheel.

In accordance with a third embodiment of the invention, needle based apparatus for isolating single fibers from a loose mass includes a sample holder which has a plate having perforations and a sample side against which a loose mass of fibrous material is pressed such that portions of the fibrous material project through the perforations, and a single-needle sampler assembly. The single-needle sampler assembly includes a needle arranged for generally parallel movement relative to the perforated plate so as to load fibers from the projecting portions onto the needle, a guide element to control the amount of fibers collected, and a fiber plate movable relative to the needle between a clamping position and a sampling position. The fiber plate has a leading edge configured for engagement with the needle so as to clamp fibers between the needle and the fiber plate leading edge in the fiber plate clamping position. In the fiber plate sampling position, the leading edge is spaced from the needle to permit the controlled loading of fibers onto the needle. Preferably, the spacing between the leading edge and the needle in the fiber plate sampling position is sufficiently close so as to minimize bunching of fibers loaded onto the needle.

The single-needle sampler assembly additionally includes a retractable fiber plate housing movable between a retracted position which exposes a working portion of the fiber plate and a sampling position which substantially encloses the fiber plate with the exception of a projecting portion immediately adjacent the leading edge. The fiber plate housing, in its sampling position, defines an air flow passage on either side of the fiber plate such that the ends of fibers loaded onto the needle are drawn into the air flow passage generally along side the fiber plate, with an intermediate portion of each fiber engaging the fiber plate leading edge.

The single-needle sampler apparatus additionally includes a beard preparation station including at least one element for combing out fibers on the fiber plate working portion while the fiber plate is in its clamping position and the fiber plate housing is in its retracted position.

Finally, there is a feeder for feeding fibers off the fiber plate working portion substantially individually into an air stream. The feeder may comprise alternatively an apron or a roll.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description, taken in conjunction with the drawings, in which:

FIG. 8 depicts the apparatus of FIG. 1 employed as a preprocessor for an AFIS machine;

FIG. 9 depicts the loading of a needle sampler in accordance with a second embodiment of the invention;

FIG. 10 is a front view of the needle sampler of FIG. 9;

FIG. 11A is an enlarged front view of a needle holder;

FIG. 11B is an enlarged side view of the needle holder;

FIG. 12 is an enlarged view of the elastomer clamping feedroll of FIG. 9;

FIG. 18 depicts the loading operation of a single-needle sampler in accordance with a third embodiment of the invention;

FIG. 19 is a front view of the single-needle sampler assembly of FIG. 17;

FIGS. 20A, 20B and 20C are enlarged top, end and side views of the single-needle sampler of FIG. 18;

FIG. 21 depicts a plurality of individual fiber samples clamped between the needle and a fiber plate and being drawn into the housing;

FIG. 22 depicts the housing retracted from the fiber plate, presenting fibers for preparation;

DETAILED DESCRIPTION

Figure 1:
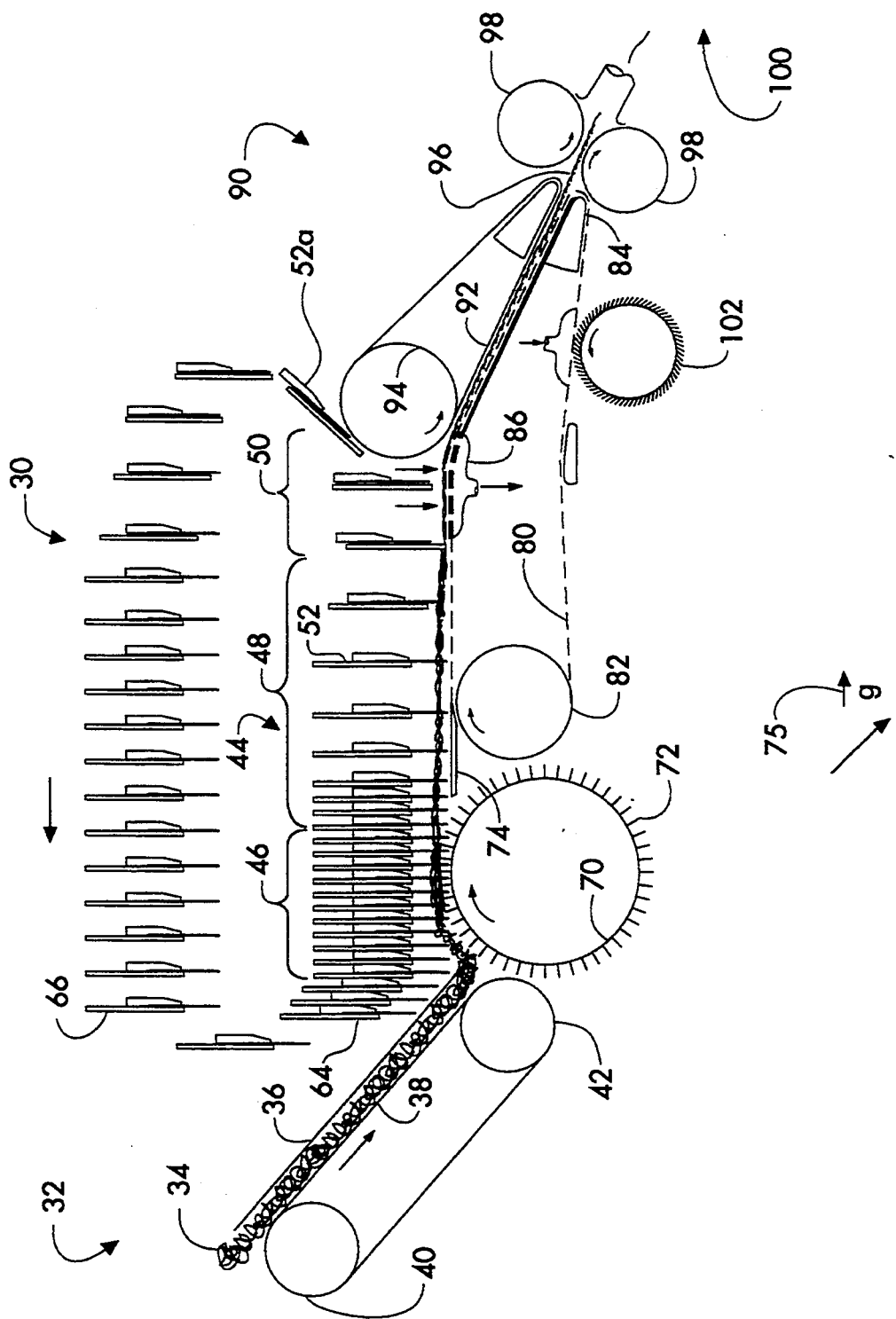
FIG. 1 depicts in overview a fiber individualizer in accordance with the first embodiment of the invention employing accelerated pin drafting.
Figure 2:
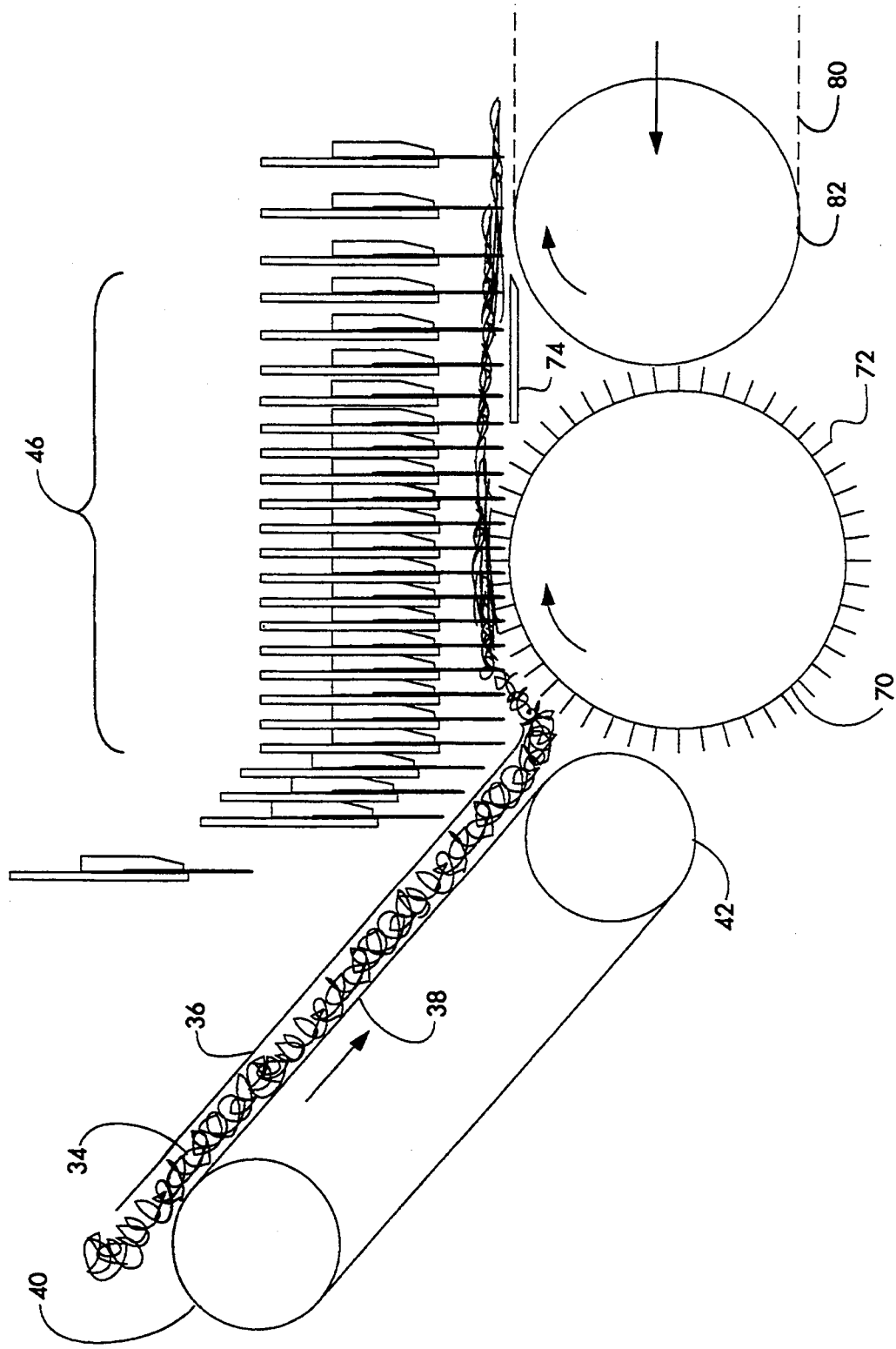
FIG. 2 is an enlargement of a portion of the FIG. 1 apparatus depicting loading of fibers into the accelerated pin drafting apparatus.
Figure 3:
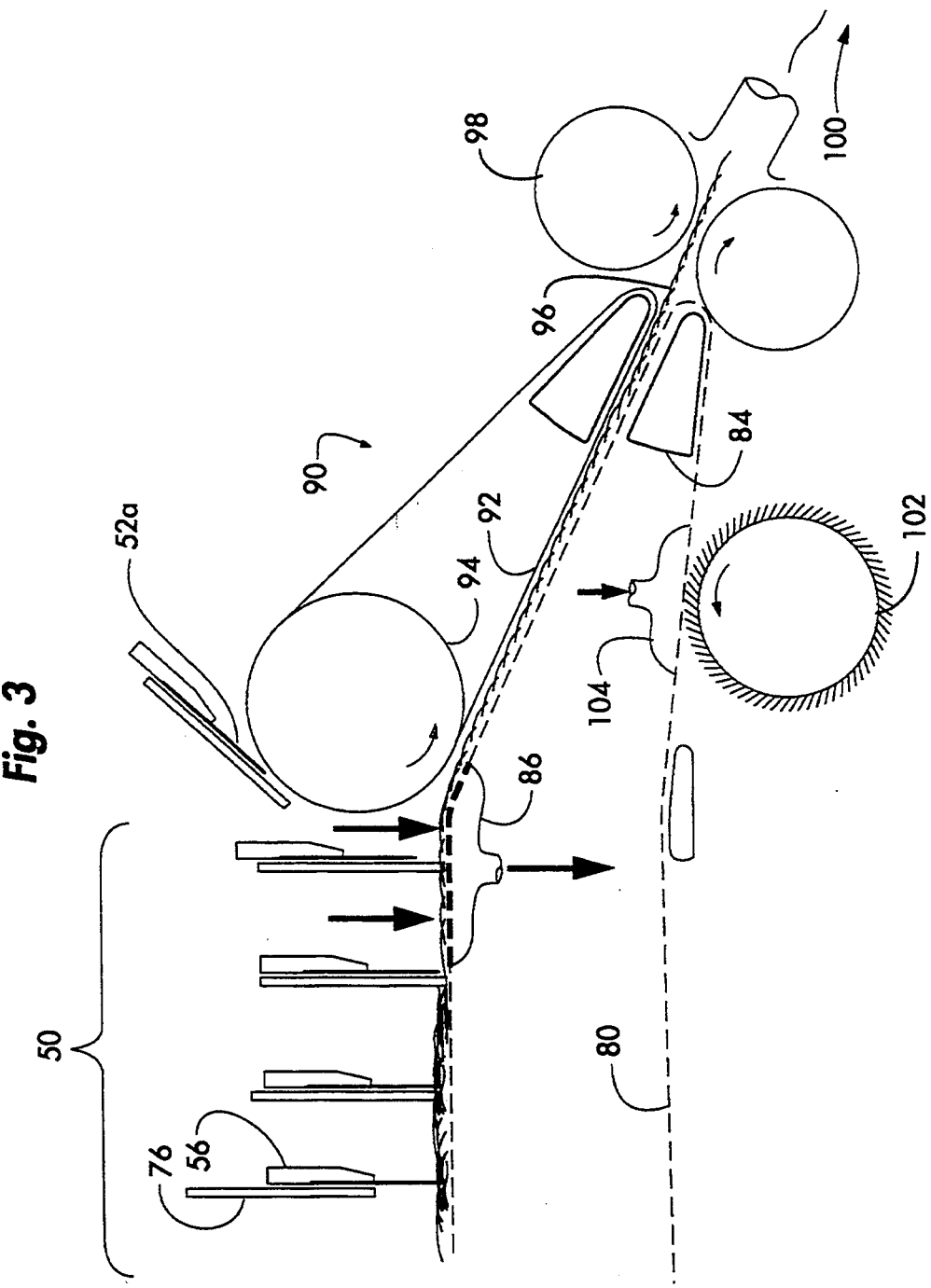
FIG. 3 is an enlargement of a portion of the FIG. 1 apparatus depicting stripping and ultradrafting.

Referring now to the drawings, FIGS. 1-8 depict needle-based apparatus in accordance with the invention for individualizing single fibers and other textile entities. FIG. 1 is an overview of one form of the apparatus, while FIGS. 2 and 3 are enlarged views of loading and stripping portions of the FIG. 1 apparatus.

The apparatus 30 includes a feed section 32 wherein fiber stock 34 is conveyed between an upper stationary feed plate 36 and a lower belt 38 carried by a pair of rolls 40 and 42. Feed section 32 may employ Test Zone Environmental Control (TZEC), as disclosed in Shofner U.S. patent application Ser. No. 07/999,226, filed Dec. 31, 1992, entitled "Direct Control of Fiber Testing or Processing Performance Parameters by Application of Controlled, Conditioned Gas Flows", the entire disclosure of which is hereby expressly incorporated by reference. In the case of TZEC, the test sample is conditioned prior to and during testing by application of condition gas flows. The fiber stock 34 is transported into a pin drafting machine, generally designated 44, including a loading section 46, a drafting zone 48, and a stripping zone 50.

Figure 4:
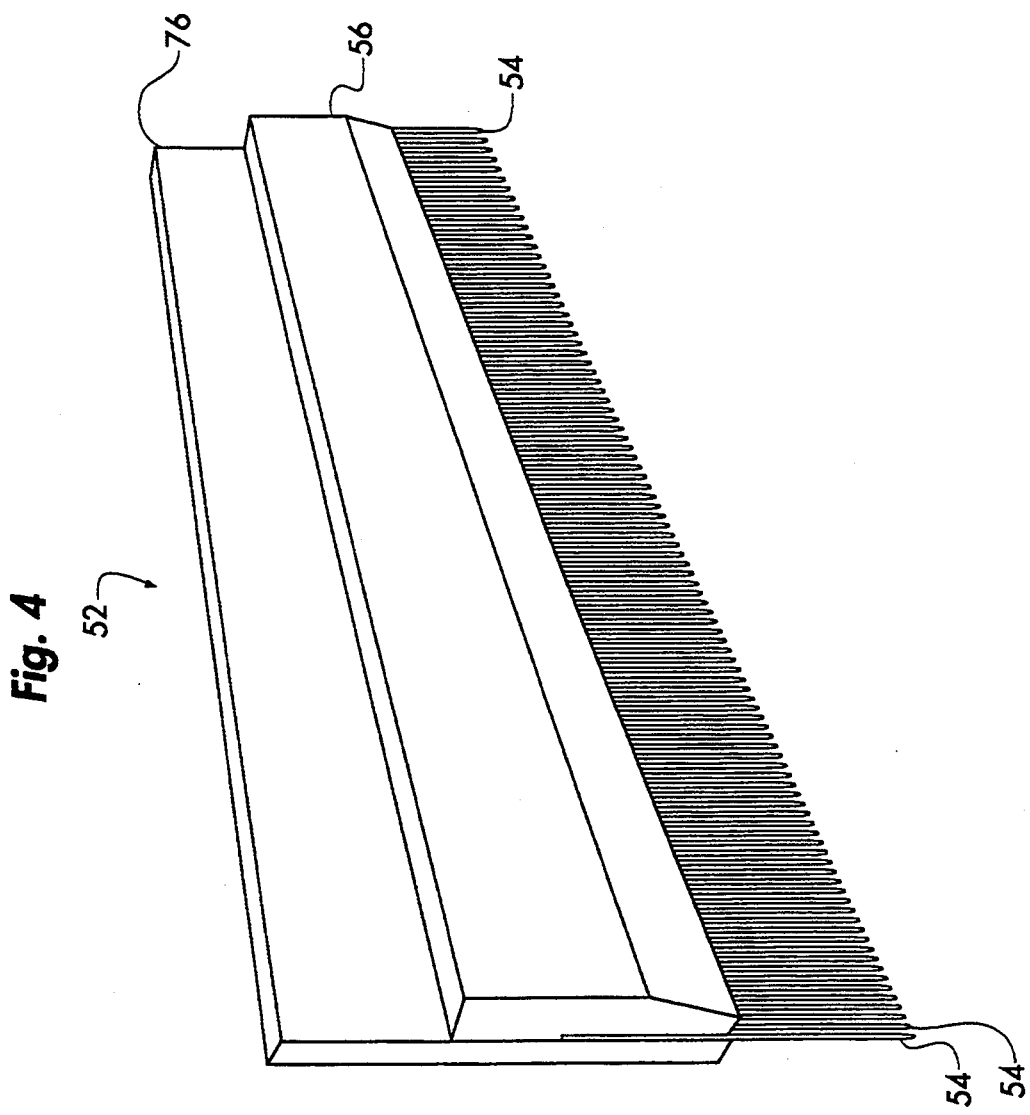
FIG. 4 is a perspective view of a single combing element.
Figure 5:
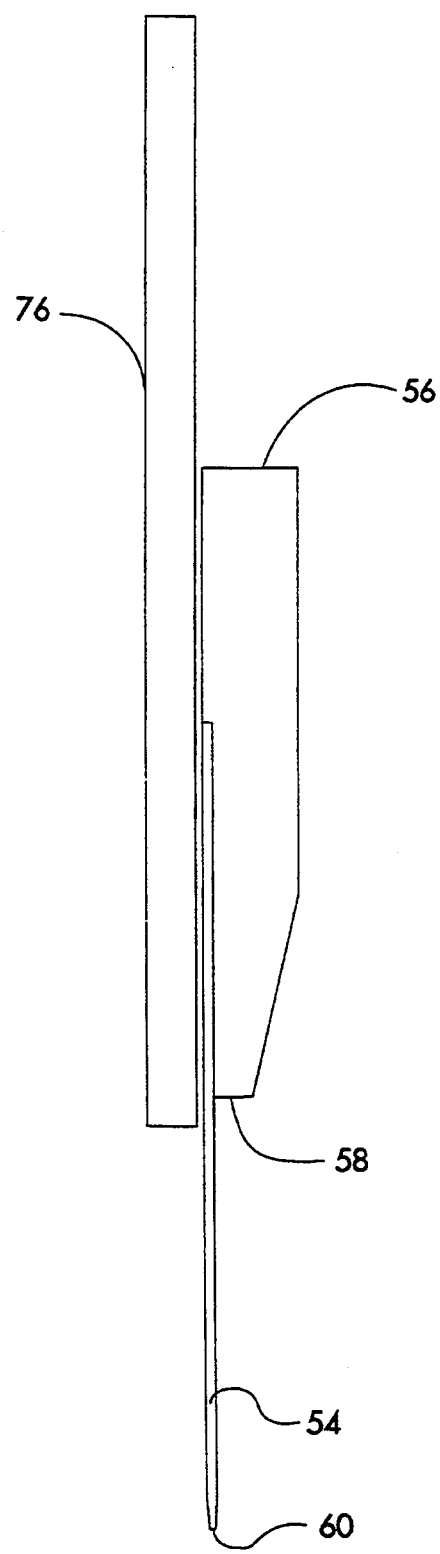
FIG. 5 is an enlarged end view of the FIG. 4 combing element.

Central to the pin drafting machine 44 are a plurality of combing elements 52 which are arranged to pierce the fiber mat 34 as it is presented at the input, and to move from input to output (left to right in FIGS. 1-3) with increasing distance between adjacent combing elements, as is described hereinbelow with particular reference to FIG. 6. FIG. 4 shows in perspective an individual combing element 52, which comprises a series of needle-like pins 54 mounted to a pin bar, while FIG. 5 is an enlarged end view of the pin bar 56 and a single needle 54. The pin bar 56 is from one to four inches wide. The individual pins 54 are approximately 0.013 inch in diameter, and have a length of approximately 0.50 inch, measured from the lower end 58 of the pin bar 56 to the tip 60 of the needle 54. The pins 54 are spaced uniformly, with a density of 62 pins per inch.

FIG. 1 conceptually illustrates the motion of the individual comb elements 52, which is similar to that of a conventional faller bar set, but with varying spacing between adjacent combing elements 52. For example, the combing elements 52 are carried counterclockwise around an oval track, with the lower row 64 of pins 52 in FIG. 1 generally corresponding to the combing elements 52 engages the fiber, and with the upper row 66 of combing elements 52 simply being returned to the starting point, having been lifted away from engagement with fiber being processed.

Figure 6:
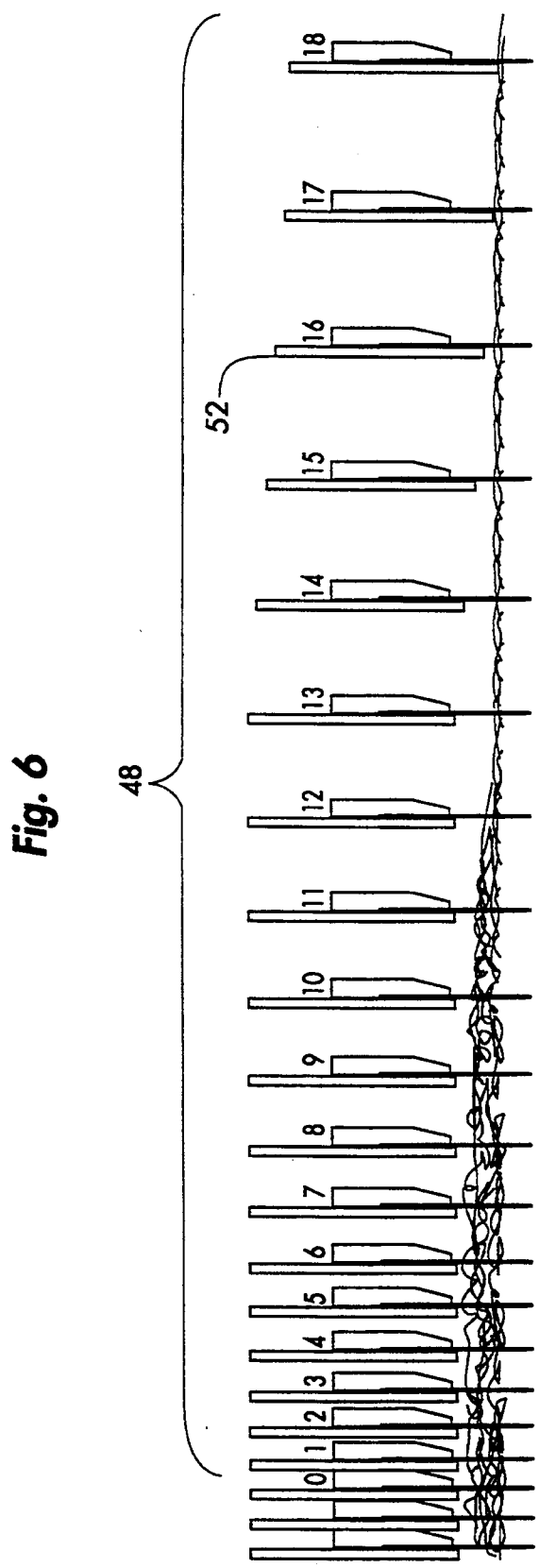
FIG. 6 graphically depicts the movement of individual combing elements.
Figure 7:
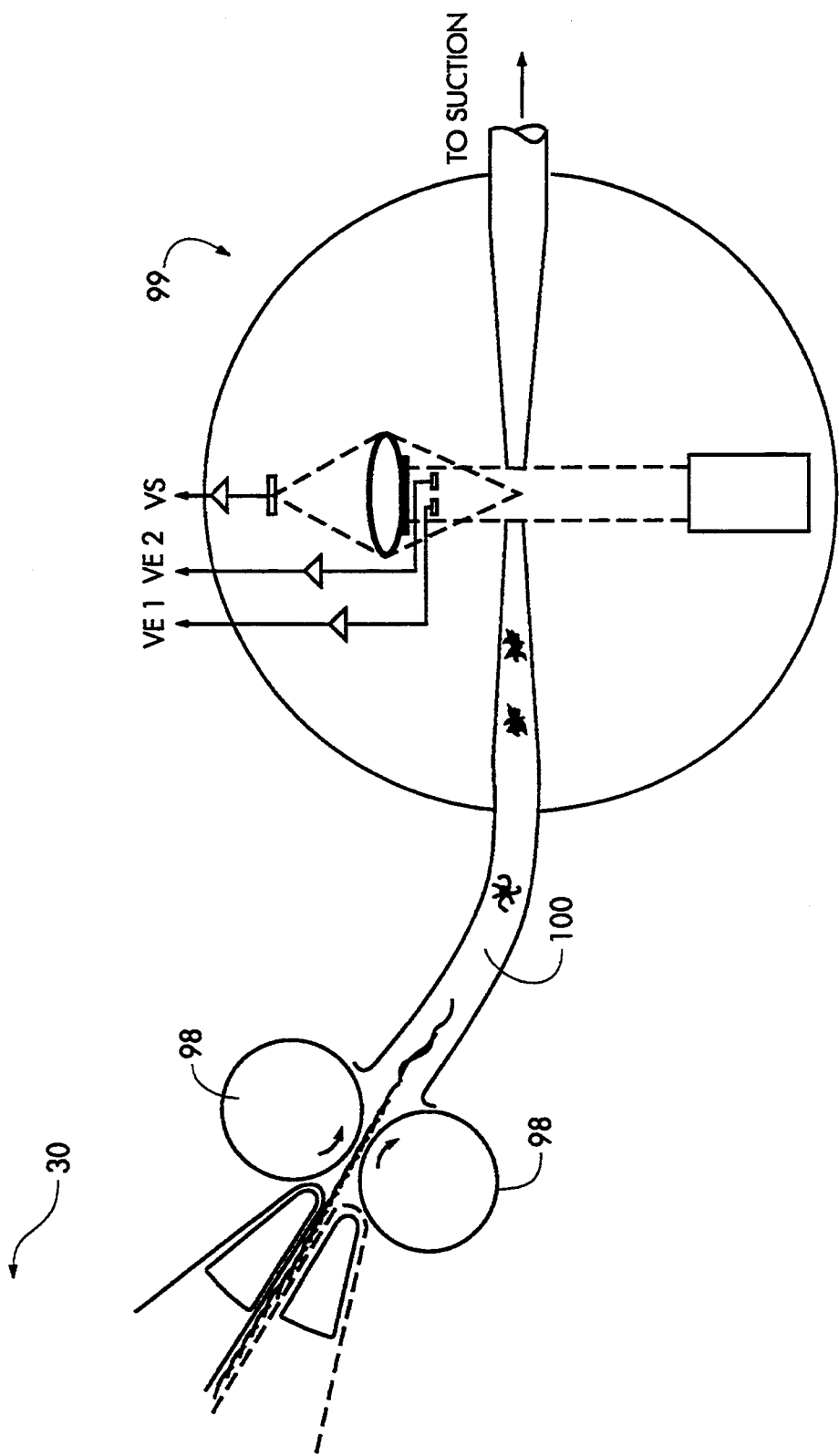
FIG. 7 depicts individualized fiber entities being supplied to a sensor.

The spacing between the combing elements 52, as they pass through the drafting zone 48 of FIG. 1, is graphically and numerically described in FIG. 6. In FIG. 6 individual combing elements are arbitrarily designated 0 through 18. Below each combing element 52 is a first number (s) giving the distance, in inches, from combing element 0 employed as a reference point, and below that a number (t) giving the time in seconds for the particular combing element to have reached the position indicated. Preferably, the process is a continuous one, and the combing elements 52 are accordingly continuously accelerating as they move from left to right. A third row of numbers (v) below the combing elements in FIG. 6 is the instantaneous velocity of each pin at the position indicated. In this example there is a constant acceleration $a = 0.0495$ in/sec$^2$.

A variety of known mechanisms may be adapted to produce the particular combing element movement depicted in FIGS. 1-3, and particularly in FIG. 6. In general, such mechanisms are known for the purpose of bi-axially stretching plastic film. One such mechanism, involving a series of individual links with rollers constrained to move between tracks of varying spacing, is disclosed in Sakakibara et al U.S. Pat. No. 3,153,812. Another approach, involving a drive screw having a groove with a pitch that increases along the length of the drive screw, is disclosed in Kamfe et al U.S. Pat. No. 4,200,963. Other examples are disclosed in Nagae et al U.S. Pat. No. 3,276,071; Tsien U.S. Pat. No. 3,427,684; Kampf Pat. U.S. No. 3,916,491 and Allen U.S. Pat. No. 4,384,392.

Referring again to FIGS. 1-3 in greater detail, FIG. 2 in particular depicts the loading section 46, which includes a cylindrical rotating wheel 70 having projections 72 which serve to push fiber stock 34 onto the pins 54 of the combing elements 52 as the stock 34 emerges from the guide plate 36 and belt 38. In the loading zone 46, in order to avoid binding or interference with the projections 72 of the wheel 70, the combing elements 52 move at a constant velocity with uniform spacing. The projections 72 may be thin plates or bars.

The fiber material then enters the drafting zone 48 of FIG. 1 which is bounded by a solid lower plate 74 or a perforated belt 80 under the drafting zone 48, such that all textile entities associated with the fiber mat, for example, fibers, neps and trash, remain with the sample to be subsequently measured. Although in FIG. 1 the lower plate 74 and direction of movement are drawn as horizontal, it will be appreciated that this is for convenience of illustration only, and that, in an actual machine, the apparatus and support plate 74 are all inclined so that gravity 75 assists the movement from left to right in the FIG. 1 orientation, and there is no accumulation of material on the lower plate 74. The lower plate 74 also blocks air currents.

In operation, each combing element 52 acts to restrain the fiber relative to those preceding (to the right) and to comb and draft the fibers relative to the following combing element 52 (to the left). Assuming for purposes of example that the spacing between adjacent combing elements 52 is 0.1 inches at the beginning of the drafting zone 48, and is 1.0 inches at the end of the drafting zone 48, the draft ratio would be ten to one. The resultant drafting and paralleling of fibers is very gentle, and results in minimal fiber breakage.

As shown in FIGS. 1 and 3, as the fiber mat leaves the drafting zone 48 and enters the stripping zone 50, the combing elements 52 are again uniformly spaced and have constant velocity. In the stripping zone 50, stripper bars 76 move down alongside the individual pins 54 so as to disengage fibers and other entities from the pins 54 of the combing elements 52. A perforated belt 80 is carried by a roller 82 and an idler bar 84 below the stripping zone 50. To aid in stripping the fiber, a manifold 86 is provided which draws air through the perforations in the belt 80. The perforations in the belt 80 are relatively small, in the order of 50 μm, such that fibers, trash and neps are generally not drawn through the perforations. (At this point there is also the opportunity to measure microdust in the air from manifold 86, generally according to Shofner U.S. Pat. No. 4,512,060.)

In an exit zone 90, an upper apron 92 is positioned above the perforated belt 80 in order to gently restrain and convey the fibers between the apron 92 and belt 80. The apron 92 is driven by a drive roll 94 as indicated.

To further aid in cleaning the combing elements 52, as indicated at 52a, the combing elements, as they are retracted (beginning their return path as depicted in FIG. 1), they are moved closely adjacent the drive roll 94 for cleaning action.

Finally, the apron 92 and belt 80 deliver the fibers at 96 to a pair of feed rolls 98 for ultradrafting. The feedrolls 98 pull fibers and other entities from the apron, and release them, substantially one at a time, into an air stream 100. At this point, the fibers and other entities are substantially individualized, and may be introduced into a suitable sensor, such as is disclosed in the above-identified Shofner et al application Ser. No. 07/962,898, filed Oct. 16, 1992, and illustrated in FIG. 7.

Although there may be employed several sets of aprons and rolls in series, the apron 90 and pinch rollers 98 comprise what may be termed an ultradrafting system, with a drafting ratio of perhaps 300. With vacuum suction employed at the exit of the pinch rollers, the net result is that single fibers and single neps or trash are released and carried out to a suitable sensor 99, starting with a mass of entangled fibers introduced at 34.

For cleaning any remaining fiber from the belt 80 there are shown in FIG. 3 a cleaning station located on its lower return path comprising a rotating brush 102 and a manifold 104 for blowing air through the perforations in the belt 80.

FIG. 8 depicts the accelerated pin drafting apparatus of FIG. 1 employed as preprocessor to an AFIS fiber individualizer, generally designated 110. It will be appreciated that the AFIS device 110 in FIG. 8 is known, being of the type disclosed in the above-identified Shofner U.S. Pat. No. 4,512,060. Very briefly, incoming fiber is engaged by protrusions on a perforated cylinder 112 rotating clockwise at approximately 7500 rpm, next engages card flats 114 and 116, and is then transferred to a solid cylinder 118. Various entities are aeromechanically released, separated, and thrown out and thus separated through counterflow slots 120 and 122, all as described in U.S. Pat. No. 4,512,060. The utility of feeding the AFIS Fiber Individualizer with the accelerating pin drafter 30 is that fiber breakage is greatly reduced.

Referring now to FIGS. 9-17, depicted is another embodiment of needle-based apparatus in accordance with the invention. The apparatus of FIGS. 9-17 is based on a Hertel needle sampler, such as is disclosed in the above-identified U.S. Pat. No. 3,057,019.

An important aspect of the Hertel sampler is passing a comb-like needle sampler past perforations in a metal plate through which the fibrous mass is pressed such that fibers of varying lengths are loaded onto the pins, and subsequently locked. In the traditional use of the Hertel sampler, the resultant tapered beard is combed, brushed and measured, all as described hereinabove. In accordance with the present invention, the fibrous material is sampled in the same way, and it has been shown that this particular sampling technique generally produces a representative sample. The present invention differs from the traditional Hertel sampler in that fibers are individually fed from the sampler for subsequent analysis.

FIG. 9 illustrates a sample holder 150, including a plate 152 having perforations 154, and a sample side 156 against which a loose mass 158 of fibrous material is pressed by a pressure plate 160. Portions 162 of the sample 158 thus project through the perforations 154. The perforations 154 are in the order of 0.63 inch in diameter, with a spacing of 0.88 inch. As may be seen in FIG. 9, the edges of the perforations 154 are rounded and smooth so as to minimize cutting and breakage of fibers as fibers are pulled through the perforations 154.

The apparatus additionally includes a comb-like needle sampler 164, shown also in FIG. 10 in front view. The needle sampler 164 includes a plurality of individual pins or needles 165. Traditionally, the needles 165 are spaced by 1/13 inch, and are about 0.02 inches in diameter. Their projected length above their mount is approximately 0.2 inches, and the overall width of the sampler in the FIG. 10 orientation is in the order of three inches. FIGS. 11A and 11B are enlarged views of the needle holder portion of the needle sampler 164.

The needle sampler 164 is arranged for generally parallel movement relative to the plate 152 so as to load fibers from the projecting portions 162 onto the individual needles or pins 165, to produce the results shown in FIG. 10. The protruding fibers are however first engaged by a guide plate 157 which facilitates control of the amount of sample collected. FIG. 10 in particular illustrates what is known in the art as a tapered beard 166 which, after combing and brushing described hereinbelow, comprises a plurality of fibers of varying lengths loaded onto the pins 165 at various intermediate points along the length of the individual fibers. This is more clearly evident in the embodiment of FIGS. 21 and 22.

In the traditional Hertel sampler, the tapered beard 166 remains locked in position for the remainder of the operation.

Instead of the threaded locking and unlocking device of the Hertel sampler, the present invention employs an element, shown in FIG. 9 as an elastomer clamping feedroll 170, which is arranged to move forward or close and thereby to selectively engage the needle elements along at least a portion of their lengths for locking loaded fibers on the needle sampler 164. The feedroll 170 is seen in the open or sampling position in FIG. 9 and in the closed position in FIG. 12. Guide 157 can move together with feedroll 170 but this is not essential.

FIG. 12 is an enlarged view of the elastomer clamping feedroll, while in closed position to engage the needles 154, to clamp the fibers 166 in place. As indicated at 172, the elastomer clamping feedroll 170 is deformed to hold fibers against the needles along a portion of the length of the needles, rather than at a single pinch point.

As indicated by the respective arrows 174 and 176, the elastomer clamping feedroll 170 is capable of both a translation motion (arrow 174) to permit clamping, and a rotation motion (arrow 176) for subsequent gentle rolling off of the fibers from the needle sampler. A suitable mounting and drive arrangement (not shown) is provided to accomplish these two motions.

Figure 13:
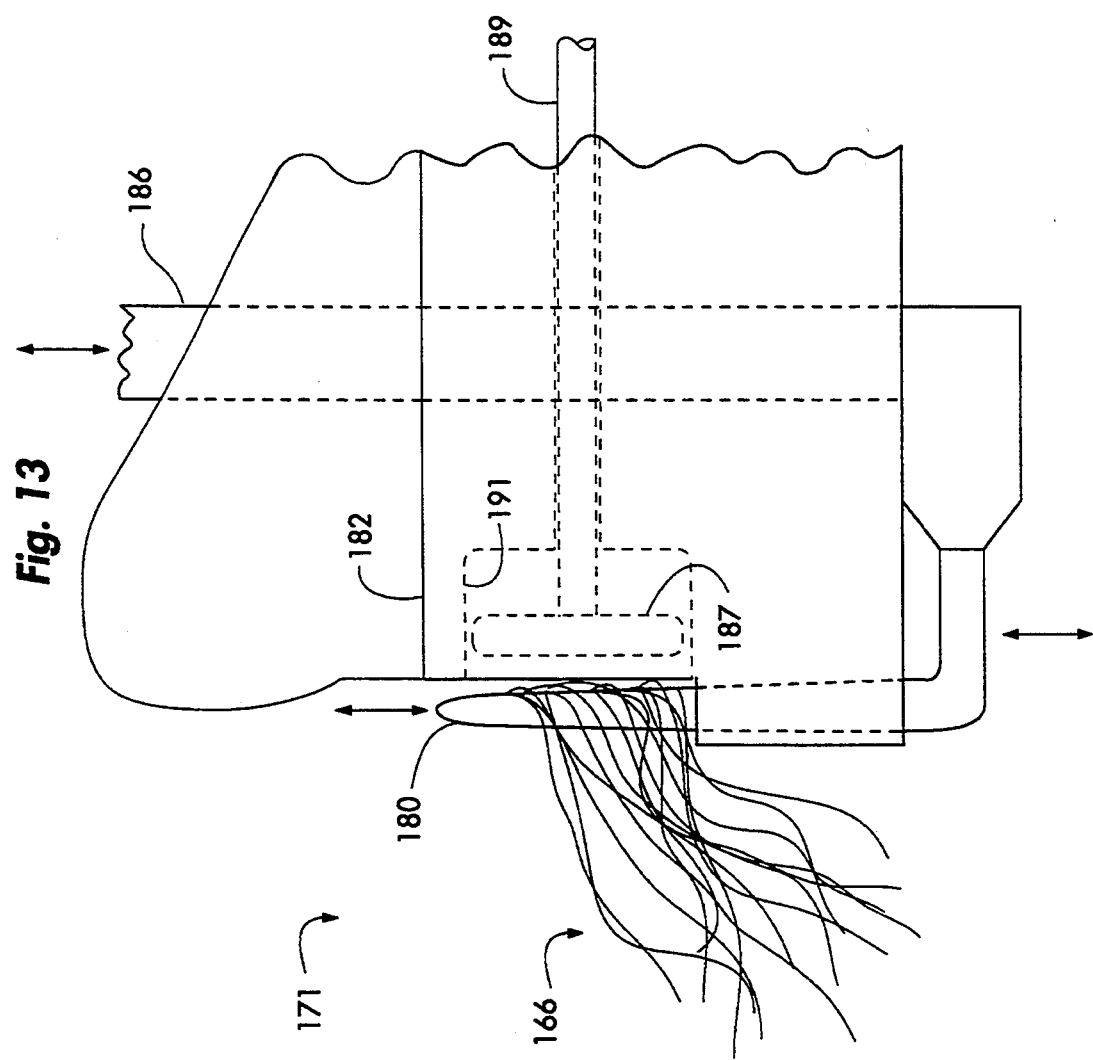
FIG. 13 depicts an alternative to the FIG. 3 elastomer clamping feedroll in the form of a retracting pin.

As an alternative to the row needle sampler 164 with elastomer feedroll 170, depicted in FIG. 13 is a retractable pin embodiment 171. In FIG. 13, a row of pins 180 is arranged like the needle sampler 164 (FIG. 10) and may, for example, also be made of stainless steel. A mounting block 182 is provided in which the needle elements 180 move downwardly, after loading, for feeding into further processing stages. The downward (and upward) movement is enabled by drive means 186. After loading but prior to moving to further processing steps, the fibers 166 are clamped against the needle elements 180 by internal elastomer bar 187. Clamping bar 187 is driven by actuator rod 189 and in machined guide-ways 191.

For subsequently slowly feeding individual fibers one at a time from the needles 180, after loading and clamping, the needles 180 may be retracted through movement of the needle holder 186 and needle 180 in a downward direction, as viewed in the FIG. 13 orientation, whereby fibers are individually released.

The arrangement of FIG. 13 thus provides for two different types of movement, one for clamping, and one for feeding.

Figure 14:
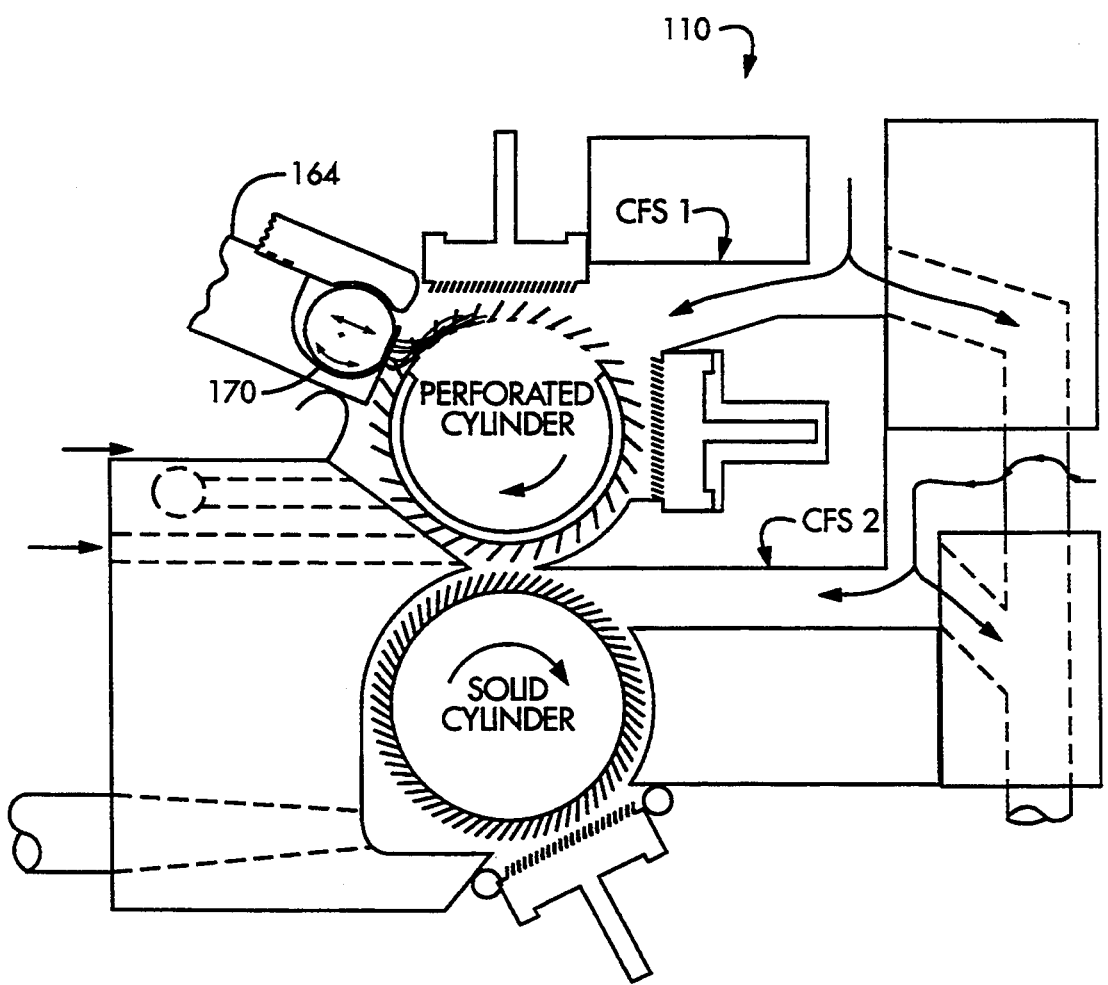
FIG. 14 depicts the needle sampler of FIG. 9 feeding an AFIS machine.
Figure 15:
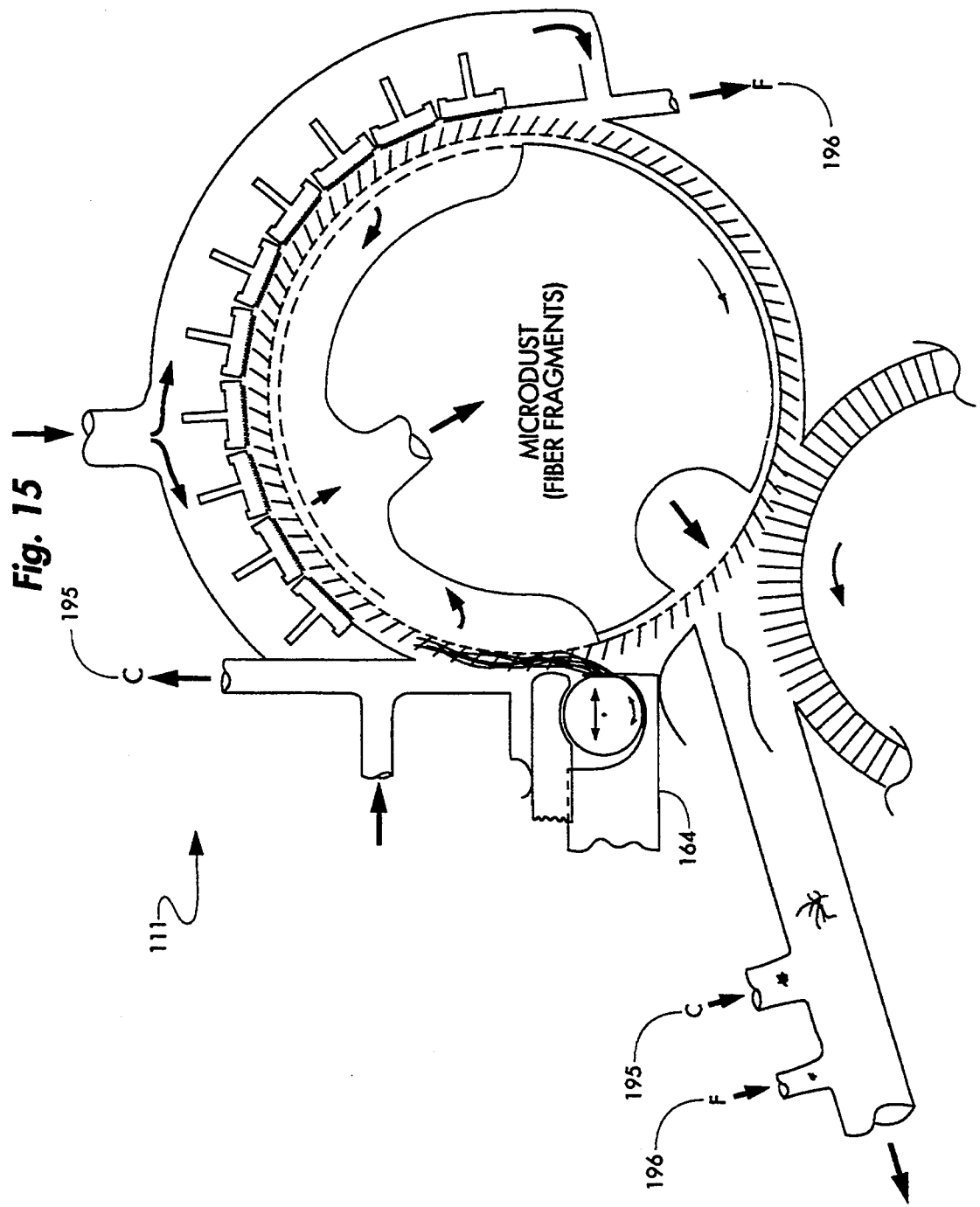
FIG. 15 is an enlarged view depicting the feeding of material into an AFIS.

FIGS. 14 and 15 illustrate the needle sampler of FIGS. 9-12, including the elastomer clamping feedroll 170, employed to feed fibers into an AFIS, substantially identical to the AFIS 110 of FIG. 8, for further individualization and testing.

FIG. 15 will be recognized as another form of the AFIS Fiber Individualizer. In this case the individualized coarse 195 and fine 196 trash separations are recombined with the individualized fibers, neps, etc. The objectives of feeding AFIS Fiber Individualizers 110 and 111 with the row needle sampler 164 or 171 are to reduce fiber damage and/or to facilitate automation. Methods and apparatus enabling the latter objective are disclosed in a copending application Ser. No. 07/999,007, filed Dec. 31, 1992, entitled "Acquisition, Measurement and Control of Thin Webs of In-Process Textile Materials".

Figure 16:
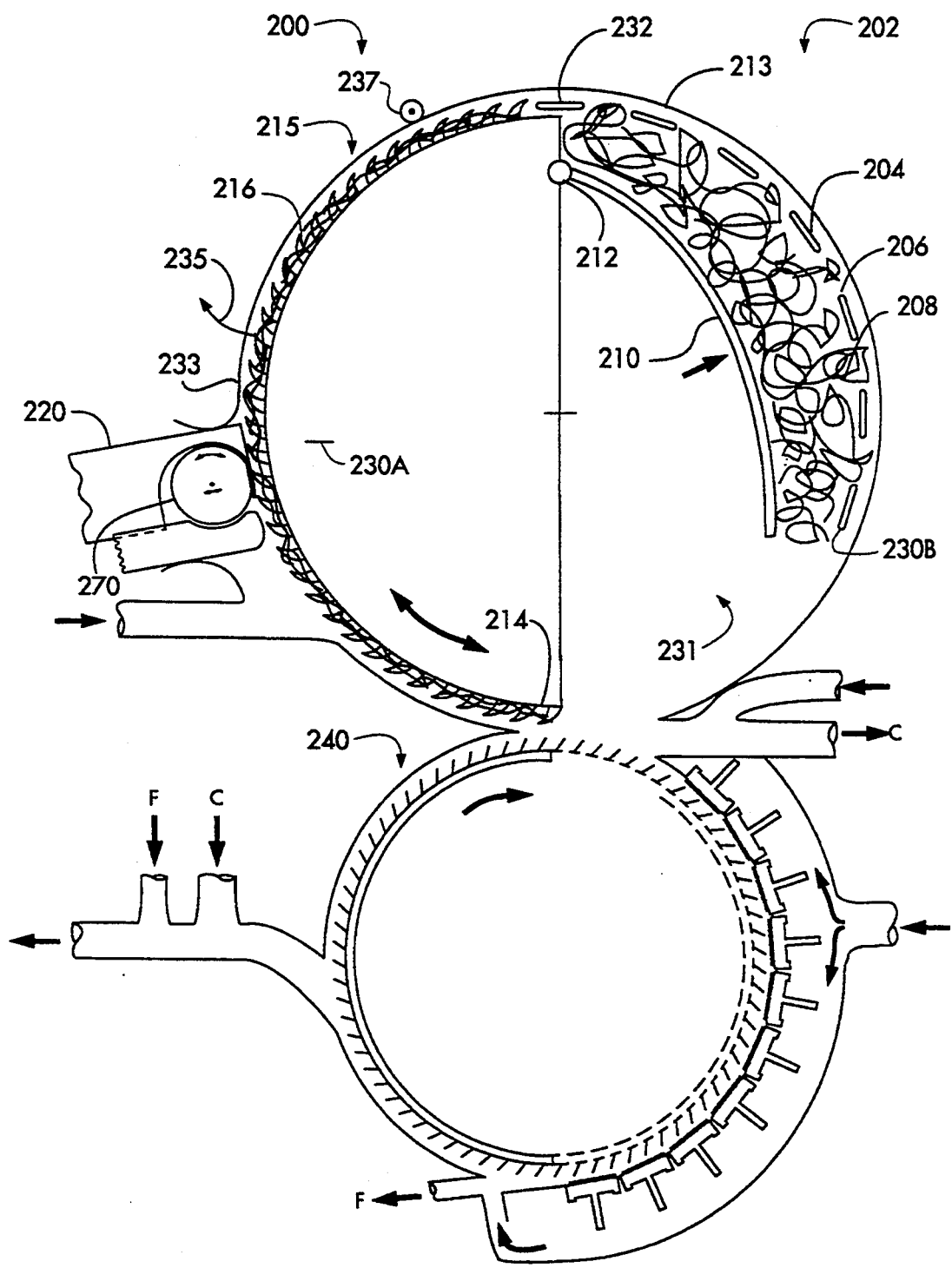
FIGS. 16 and 17 are alternative forms of the needle sampler based on a modified "bucket" sampler.

FIG. 16 depicts a modification of a Hertel needle sampler, as embodied in a Model 900A High Volume Instrument (HVI), manufactured by Zellweger Uster, Inc., Knoxville, Tenn. More particularly, the sampling drum 200 and operational steps are modified in accordance with the invention to achieve fiber individualization and automation.

The apparatus of FIG. 16 includes a known apparatus 200 in the general form of a cylindrical drum which is rotatable about its axis, and which is at least partially hollow for receiving a sample. The drum is approximately twelve inches in diameter and 5.5 inches in width and rotates within a housing 213. The drum 200 includes a sample holder portion 202 including a circumferential cylindrical wall segment 204 with perforations 206 against which a loose mass of fibrous material 208 to be sampled is pressed from the inside, such that portions of the fibrous material 208 project through the perforations 206. A plate 210 pivotally mounted at 212 provides pressure on the sample 208.

The drum 200 additionally includes a card doffer wire portion 215 including a circumferential segment having doffer wire 216 projecting radially outwardly.

Also provided is a comb-like needle sampler 220, substantially like the needle sampler 164 of FIG. 9, positioned adjacent to the drum 200 such that fibers projecting through the perforations 206 are loaded onto the needle sampler 220 as the cylindrical wall segment of the sample holder rotates in a first clockwise direction past the needle sampler.

In the operation of the drum 200 as thus far described, the drum is initially rotationally oriented with the sample opening 231 adjacent reference mark 230A. That is, points 230A and 230B are in juxtaposition. The cover 233 is hinged at 237 and is opened in the direction of the arrow 235 and a sample 208 is placed within the sample holder. The cover 233 is then closed and the drum 200 is rotated in a clockwise direction such that the perforations 206 move past the needle sampler, loading fiber onto the needles, in the same manner as depicted hereinabove with reference to FIG. 9. After loading, the elastomer clamping feedroll 270 is then moved against the needles, in the position illustrated, to clamp the sample. At this stage, point 232 on the drum 00200 is positioned near the needle sampler 220 or reference mark 230A.

The remaining operation differs substantially from the conventional Hertel sampler as embodied, for example, in the model 900A drum. In particular, in the model 900A drum as conventionally employed, as the drum continues to rotate, the card doffer wire 216 combs the tapered beard which is locked onto the needle sampler. This combing action has the effect of removing loose fibers and trash from the tapered beard such that a tapered beard of initially 0.5 gram, for example, is reduced to about 0.1 to 0.2 gram. In the conventional device, the tapered beard is then removed for further Fibrograph testing as described hereinabove in the "Background" section.

In accordance with the present invention, rather than holding the tapered beard for combing, as the bucket 200 continues to rotate clockwise, carrying the doffer wire past the needle sampler, the elastomer clamping feedroll 270 rotates in a clockwise direction as indicated to slowly feed all of the fiber from the needle sampler onto the doffer wire. Ideally, 100% of the collected fiber sample is deposited uniformly on the doffer wire 216, and preferably this is a heavier sample, for example, 1.0 gram.

At this point, the sampler 220 is retracted and drum 202 is rotated in the counterclockwise direction, and fiber on the doffer wire is fed to the cylindrical rotating beater wheel of an AFIS machine 240, for individualizing and testing as already described hereinabove.

Figure 17:
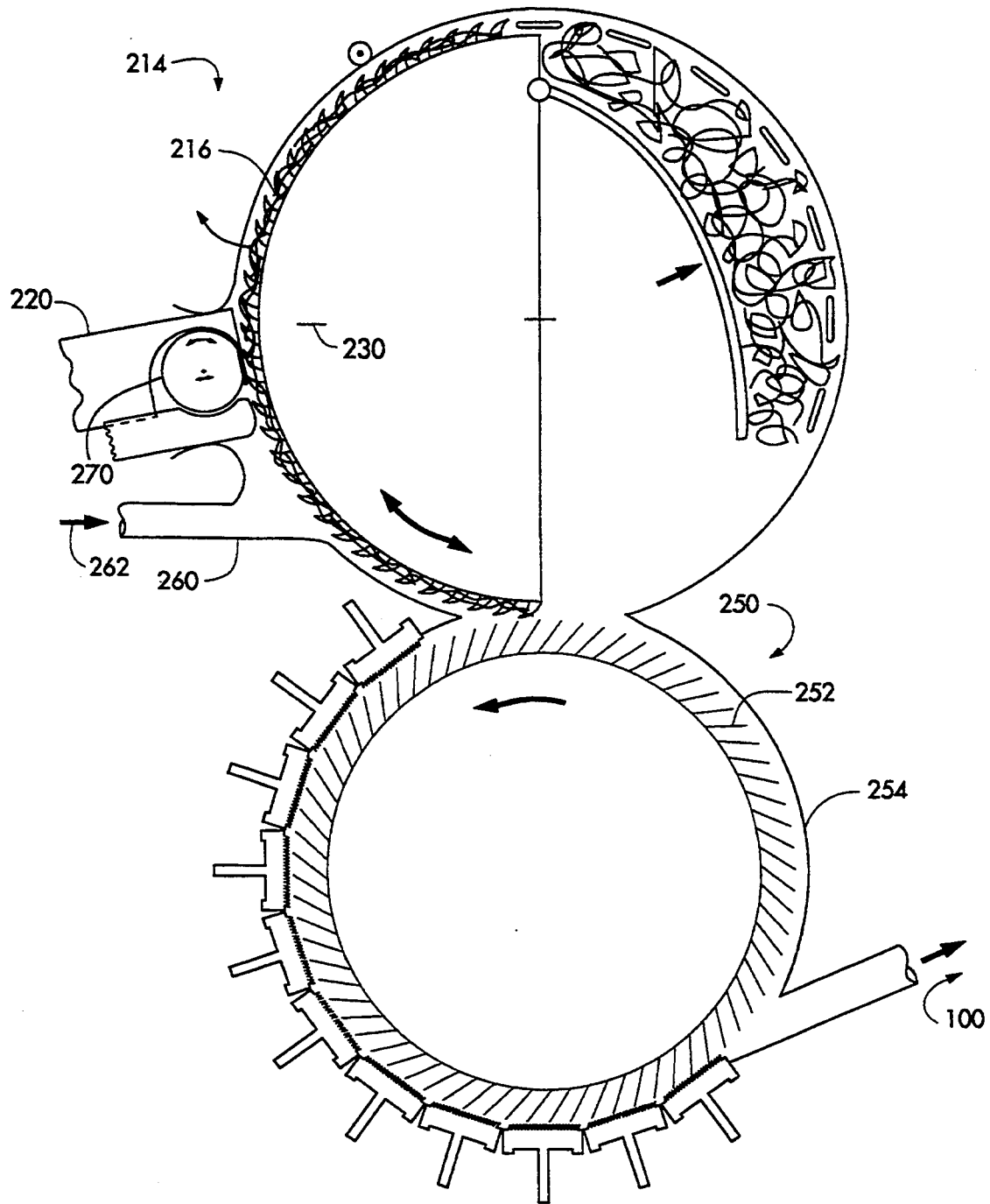
Figure 20A:
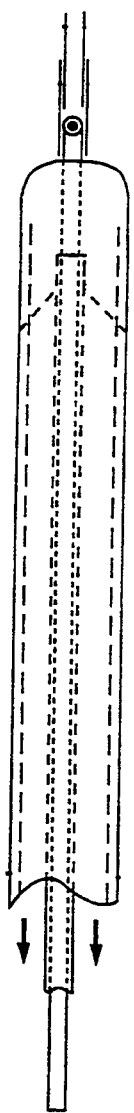
Figure 20B:
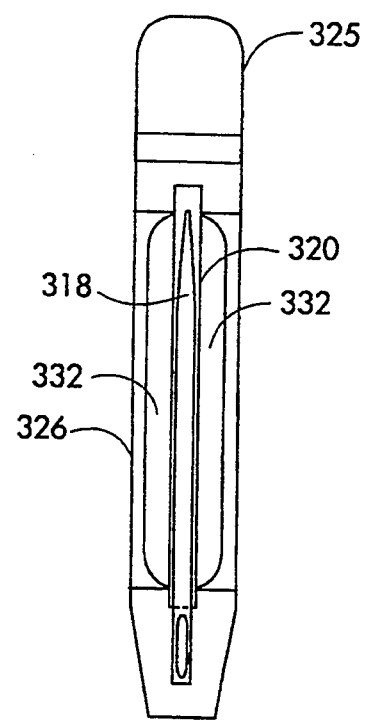

The needle sampler 164 and 171 can thus advantageously feed textile entity samples to an AFIS system in FIGS. 14 or 15 or can feed the HVI 900A drum of FIG. 16 which in turn feeds an AFIS system. It will be appreciated that the needle sampler 220, in combination with the uniform loading into and combing and individualization action by the doffer wire 216 can also directly feed an AFIS sensor 99 (FIG. 7) as depicted in FIG. 17. In FIG. 17, a rotary brush 250 individually removes the entities from doffer wire 216. The entities are collected by air flow 100, similarly as in FIG. 1, and then transported to AFIS sensor 99 for measurement, similarly as in FIG. 7. Brush 250 has backward inclined bristles 252 which are about 0.75 inches long and made preferably of nylon. Brush 250 diameter is about 6 inches and rotational speed is about 3000 RPM. Brush 251 moves within housing 254.

The 900A drum 200 and brush 250 are sealed except at 260, where the airflow 262 enters in response to the AFIS sensor airflow 100.

FIGS. 18–25 illustrate a third embodiment of the invention involving a single-needle sampler. It should be mentioned that, although multiple single-needle samplers may be simultaneously employed, unlike the comb-like structure of the Hertel needle sampler as described hereinabove, the needles are sufficiently far apart such that there is no interaction between the individual needles, and hence less fiber entanglement.

Referring to FIG. 18 in detail, as in the previous embodiment there is a sample holder 300 including a plate 302 having perforations 304, and a sample side 306 against which a loose mass 308 of fibrous material is pressed by means of a pressure plate 310 such that portions 312 of the fibrous material 308 project through the perforations 304.

A single needle sampler, generally designated 316, includes a needle 318 arranged for generally parallel movement relative to the plate 302 so as to load fibers from the projecting portions 312 onto the needle 318 as shown in FIG. 18.

The needle sampler assembly 316 additionally includes a fiber plate 320 movable relative to the needle between a clamping position (FIGS. 21 and 22) and a sampling position (FIG. 18). The fiber plate 320 has a leading edge 322 configured for engagement with the needle 318 so as to clamp fibers between the needle 318 and the leading edge 322 in the fiber plate clamping position, and to permit the loading of fibers onto the needle in the sampling position. Leading edge 322 may be elastomer material. In the sampling position illustrated in FIG. 18, a space 324 is defined between the leading edge 322 and the needle 318 so as to minimize bunching of fibers as they are loaded onto the needle 318.

The needle sampler assembly additionally includes a retractable fiber plate housing 326, which is hollow, and is movable between a retracted position (FIG. 22) which exposes a working portion 328 of the fiber plate 320, and a sampling position (FIGS. 18 and 20C) which substantially encloses the fiber plate 320, with the exception of a guide portion 325 immediately above and adjacent the leading edge 322.

In the sampling position of the fiber plate housing 326, air flow passages 332 (FIG. 20B) are defined on either side of the fiber plate 320 such that the ends of fibers loaded onto the needle 318 are drawn into the air flow passages generally alongside the fiber plate 320, as represented by fibers 329 in FIG. 18, with an intermediate portion of each fiber engaging the fiber plate leading edge 322. "Splitter" air flow 333 is delivered to the front of the needle sampler by conduit 335 inside actuator bar 337. This air is discharged from hole 339 and splits the two fiber ends so that they enter the proper passage 332.

Thus, during the loading operation depicted in FIG. 18, fibers are loaded onto the needle 318, in a somewhat tangled manner, represented in FIG. 19. As each individual fiber is pulled completely free from one of the perforations 304, the ends thereof are drawn into the passages 332 alongside the fiber plate 320. Although the fibers 329 are not completely untangled, at this point they are relatively straight.

Figure 23A:
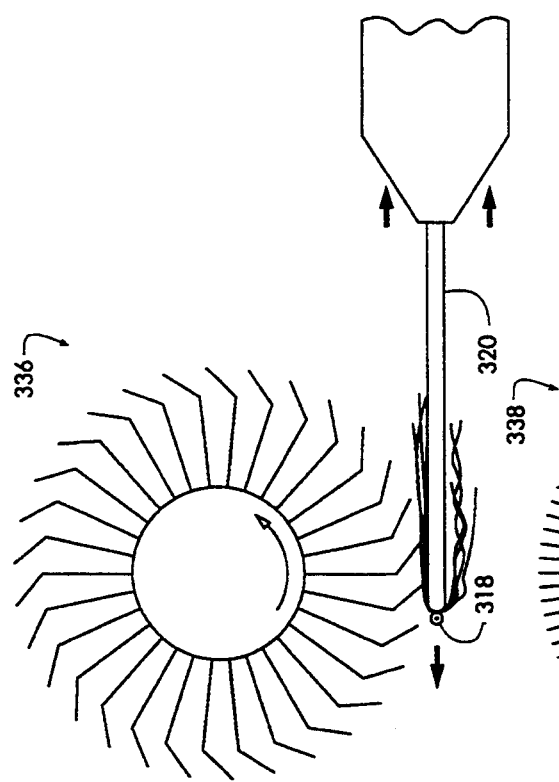
FIGS. 23A and 23B depict combing and brushing operations.
Figure 23B:
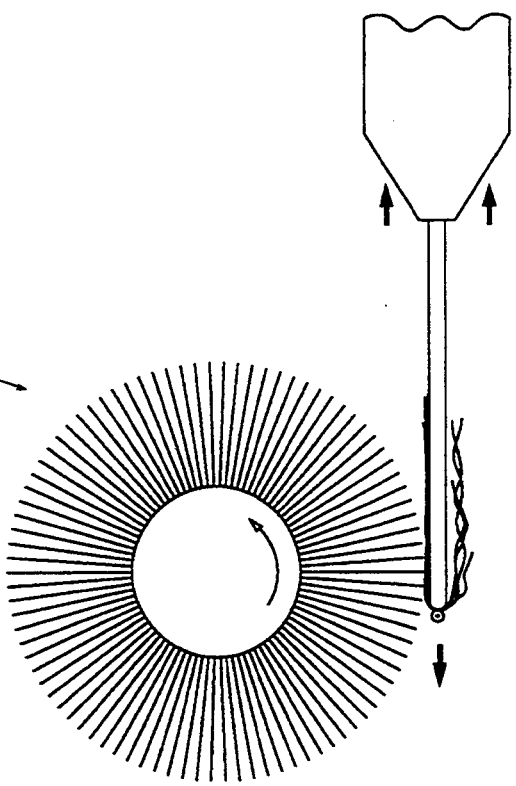

Illustrated in FIGS. 23A and 23B is a beard preparation station including a combing element 336 (FIG. 23A) and a brushing element 338 (FIG. 23B). During combing and brushing, the housing is in its retracted position, exposing the working portion of the fiber plate.

The combing and brushing operations depicted are quite similar to what is conventionally done when using a Hertel needle sampler in preparation for fibrograph testing. The purpose is to comb away excess and to remove crimp from the fibers. As clearly evident in FIGS. 23A and 23B, during this fiber preparation the needle 318 is clamped against the fiber plate 320.

Figure 24:
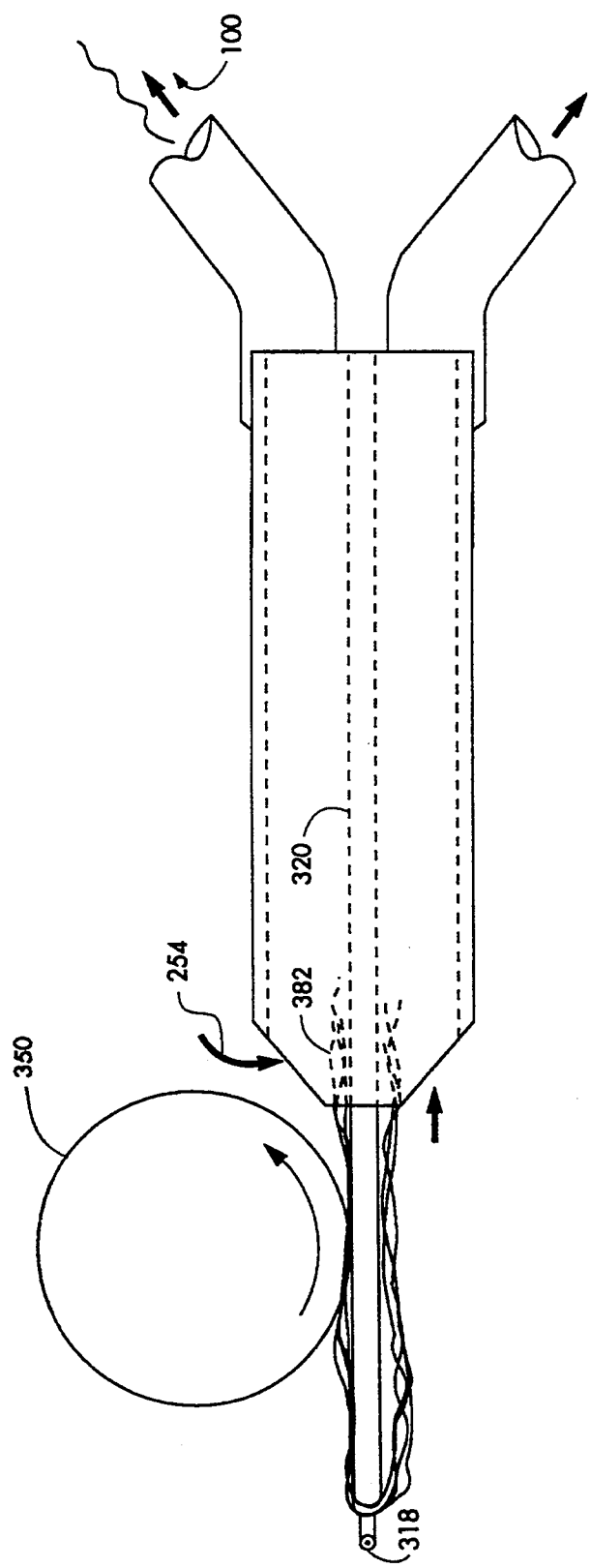
FIG. 24 depicts a roll feeder for feeding individual fibers off of the fiber plate into an air stream.

FIG. 24 depicts a roll feeder wherein a roll 350 is employed to roll fiber 382, substantially one at a time, off of the fiber plate into an airstream 100. The needle 318 is unclamped.

Figure 25:
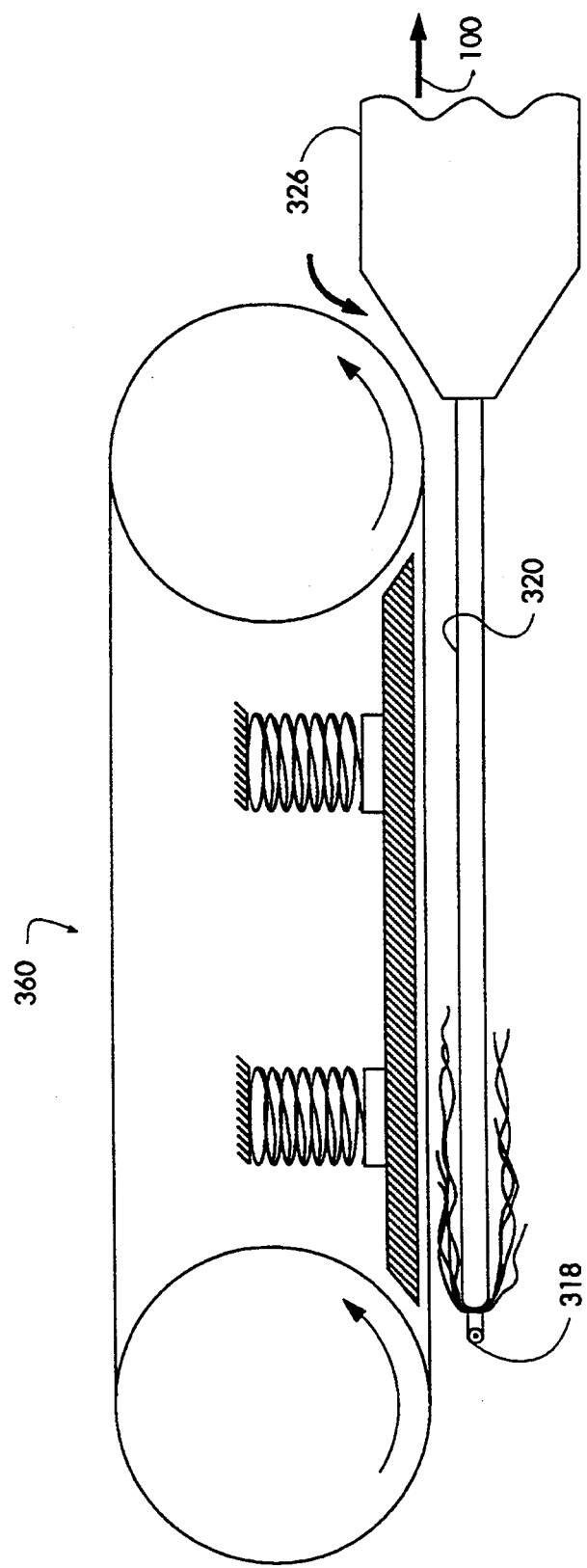
FIG. 25 similarly depicts an apron feeder for feeding individual fibers off of the fiber plate into an air stream.

FIG. 25 is similar, except that an apron feeder is employed, housing 326 is retracted, and the needle 318 is unclamped. In both embodiments illustrated in FIGS. 24 and 25, the individualized fibers are transported by airflow 100 to an AFIS sensor 99, as in FIG. 7.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. Needle-based apparatus for sampling entities included in a mass of fibrous material, said apparatus comprising:
    a drum in the form of an at least partially hollow cylinder rotatable about an axis, said drum in turn comprising:
        a sample holder portion including a circumferential cylindrical wall segment having perforations and an interior side against which a mass of fibrous material is pressed such that portions of the fibrous material project radially outwardly through said perforations, and
        a combing portion including a circumferential segment having card doffer wire on a surface of said circumferential segment projecting radially outwardly;
    a needle sampler having a plurality of needle elements positioned adjacent said drum such that entities from the projecting portions are loaded onto said needle sampler as said cylindrical wall segment of said sample holder portion rotates in a first direction past said needle sampler;
    an element arranged to selectively engage said needle elements along at least a portion of their lengths for clamping loaded entities on said needle sampler and for permitting subsequent gradual release of individual entities from said needle sampler onto said card doffer wire as said circumferential segment of said card doffer wire portion rotates in the first direction past said needle sampler.

2. Apparatus in accordance with claim 1, wherein said element arranged to selectively engage said needle elements along at least a portion of their lengths for locking loaded entities onto said needle sampler and for permitting subsequent gradual release of individual entities from said needle sampler comprises an elastomer clamping feedroll which moves against said needle elements and subsequently rotates to feed entities from said needle elements.

3. Apparatus in accordance with claim 1, which further comprises means for removing entities from said card doffer wire.

4. Apparatus in accordance with claim 1, which further comprises a cylindrical rotating beater wheel positioned adjacent said drum and having projections for engaging and removing entities from said card doffer wire as said card doffer wire portion rotates in a second direction past said cylindrical rotating beater wheel.

5. Apparatus in accordance with claim 4, wherein said element arranged to selectively engage said needle elements along at least a portion of their lengths for clamping loaded entities on said needle sampler and for permitting subsequent gradual release of individual entities from said needle sampler comprises an elastomer clamping feedroll which moves against said needle elements for locking loaded entities and subsequently rotates to feed entities from said needle elements.

6. Apparatus in accordance with claim 4, wherein said cylindrical rotating beater wheel comprises an input element of an instrument for measuring entity characteristics in fibrous samples.

7. Needle-based apparatus for sampling entities included in a mass of fibrous material, said apparatus comprising:
    a sample holder including a wall having perforations and a sample side against which a mass of fibrous material is pressed such that portions of the fibrous material project through said perforations;
    a needle sampler having a plurality of needle elements and arranged for movement relative to said wall on the other side of said wall so as to load entities from the projecting portions onto said needle sampler; and
    an element arranged to selectively engage said needle elements along at least a portion of their lengths for clamping loaded entities onto said needle sampler and for permitting subsequent gradual release of individual entities from said needle sampler.

8. Apparatus in accordance with claim 7, wherein said element arranged to selectively engage said needle elements along at least a portion of their lengths for clamping loaded entities onto said needle sampler and for permitting subsequent gradual release of individual entities from said needle sampler comprises an elastomer clamping feedroll which moves against said needle elements and subsequently rotates to gradually feed entities from said needle elements.

9. Apparatus in accordance with claim 7, wherein said element arranged to selectively engage said needle elements along at least a portion of their lengths for clamping loaded entities on said needle sampler and for permitting subsequent gradual release of individual entities from said needle sampler comprises a clamping block which moves relative to said needle elements against said needle elements for clamping loaded entities, and wherein said needle elements subsequently retract to gradually release entities.

10. Apparatus in accordance with claim 1, wherein said needle elements are flexible.

11. Apparatus in accordance with claim 7, which further comprises a cylindrical rotating beater wheel having projections for engaging entities as they are released from said need sampler.

12. Apparatus in accordance with claim 11, where in said element arranged to selectively engage said needle elements along at least a portion of their lengths for clamping loaded entities onto said needle sampler and for permitting subsequent gradual release of individual entities from said needle sampler comprises an elastomer clamping feedroll which moves against said needle elements for clamping loaded entities and subsequently rotates to feed entities from said needle elements onto said rotating beater wheel.

13. Apparatus in accordance with claim 11, wherein said cylindrical rotating beater wheel comprises an input element of an instrument for measuring entity characteristics.

* * * * *